US006164125A

United States Patent [19]
Kawase et al.

[11] Patent Number: 6,164,125
[45] Date of Patent: Dec. 26, 2000

[54] DETECTION OF MALFUNCTION IN GAS CONCENTRATION DETECTION SYSTEM

[75] Inventors: Tomoo Kawase, Nagoya; Eiichi Kurokawa, Okazaki; Yukihiro Yamashita, Kariya; Satoshi Haseda, Okazaki; Toshiyuki Suzuki, Handa, all of Japan

[73] Assignee: Denso Corporation, Kariya, Japan

[21] Appl. No.: 09/055,784

[22] Filed: Apr. 7, 1998

[30] Foreign Application Priority Data

Apr. 23, 1997 [JP] Japan ................................ 9-105966
Apr. 23, 1997 [JP] Japan ................................ 9-106159
Feb. 4, 1998 [JP] Japan ............................... 10-023600

[51] Int. Cl.[7] ........................................................ G01M 19/00
[52] U.S. Cl. ........................ 73/118.1; 73/23.32; 60/277; 701/34; 701/109
[58] Field of Search .................. 73/23.31, 23.32, 73/118.1; 701/103, 104, 109, 29, 34, 35; 60/276, 277

[56] References Cited

U.S. PATENT DOCUMENTS

| | | | |
|---|---|---|---|
| 4,356,065 | 10/1982 | Dietz | 123/489 |
| 4,561,402 | 12/1985 | Nakano et al. | 123/489 |
| 4,938,196 | 7/1990 | Hoshi et al. | 123/489 |
| 5,245,979 | 9/1993 | Pursifull et al. | 123/690 |
| 5,285,762 | 2/1994 | Werner et al. | 123/60 |
| 5,327,780 | 7/1994 | Entemann et al. | 73/118.1 |
| 5,454,259 | 10/1995 | Ishii et al. | 73/118.1 |
| 5,758,492 | 6/1998 | Kato et al. | 60/277 |
| 5,781,878 | 7/1998 | Mizoguchi et al. | 701/109 |

FOREIGN PATENT DOCUMENTS

| | | |
|---|---|---|
| 63-117251 | 5/1988 | Japan . |
| 2-204647 | 8/1990 | Japan . |
| 6-102241 | 4/1994 | Japan . |
| 2301901A | 12/1996 | United Kingdom . |

*Primary Examiner*—George Dombroske
*Attorney, Agent, or Firm*—Nixon & Vanderhye P.C.

[57] ABSTRACT

A gas concentration sensor voltage and current (in both heater on and heater off states) are detected and compared with predetermined thresholds, respectively, by a microcomputer. Based on a combination of the comparison results, the presence or absence of trouble in the system is detected and trouble location in the system is specified. In addition or alternatively, the sensor voltage is compared with thresholds to determine whether it is outside of a normal zone. The voltage may be actually detected or calculated. If the voltage is outside the normal zone, sensor voltage is reduced to zero or restricted to a predetermined limit.

19 Claims, 21 Drawing Sheets

FIG. 15

|  | TROUBLE PART & MODE | HEATER-ON | | HEATER-OFF | |
|---|---|---|---|---|---|
|  |  | Von | Ion | Voff | Ioff |
| NORMAL |  | 11V $(R_1/R_2) \cdot V_h$ | 5A $V_B/R_h$ | 0V | 0A |
| TROUBLE | A-PART OPENING | 0V | 0A | 0V | 0A |
|  | B-PART OPENING | 0V | 5A | 0V | 0A |
|  | C-PART OPENING | 12V $(R_1/R_2) \cdot V_B$ | 0A | 9V $\frac{R_1}{R_1+R_2} \cdot V_B$ | 0A |
|  | D-PART OPENING | ↑ | ↑ | ↑ | ↑ |
|  | E-PART OPENING | 9V $\frac{R_1}{R_1+R_2} \cdot V_B$ | 5A | 9V $\frac{R_1}{R_1+R_2} \cdot V_B$ | 0A |
|  | F-PART OPENING | 0V | 0A | 0V | 0A |
|  | G-PART OPENING | ↑ | ↑ | ↑ | ↑ |
|  | SHORT-CIRCUITING BETWEEN D,E,F-GND | 12V $(R_1/R_2) \cdot V_B$ | 0A | 12V $(R_1/R_2) \cdot V_B$ | 0A |
|  | CONTINUED MOS-ON | 11V $(R_1/R_2) \cdot V_h$ | 5A | 11V $(R_1/R_2) \cdot V_h$ | 5A |
|  | CONTINUED MOS-OFF | 0V | 0A | 0V | 0A |

DETECTION OF MALFUNCTION IN GAS CONCENTRATION DETECTION SYSTEM

CROSS REFERENCE TO RELATED APPLICATION

This application relates to and incorporates herein by reference Japanese Patent Applications No. 9-105966, filed on Apr. 23, 1997, No. 9-106159 filed on Apr. 23, 1997 and No. 10-23600 filed on Feb. 4, 1998.

BACKGROUND OF THE INVENTION

The present invention relates to an apparatus and method for detecting a malfunction in a gas concentration detection system, for instance, in an oxygen concentration detection system for an internal combustion engine.

In an engine mounted on a vehicle, a linear air-fuel ratio sensor (an oxygen responsive limit-current type A/F sensor) is used for detecting the air-fuel ratio of air-fuel mixture gas supplied to the engine linearly over a wide air-fuel ratio zone. It is necessary to maintain temperature of the sensor to a predetermined activation temperature in order to detect the air-fuel ratio (concentration of oxygen in exhaust gas) with high accuracy. For this purpose, the sensor is generally provided with a heater and the on-state of the heater (electric power supply to heater) is controlled by a duty ratio control signal.

According to Japanese Patent Application Laid-Open No. 5-195843 (U.S. Pat. No. 5,327,780), a voltage applied to the heater of the A/F sensor is measured during both the on-state and off-state of the heater so that a trouble (malfunction) signal is generated when the difference between the measured voltages lies outside of a predetermined range. In this apparatus, however, since it is constructed mainly to discriminate the presence or absence of trouble on the basis of voltage values (power source voltages) applied to the heater, it is insufficient to specify the trouble part in the heater control system in a trouble mode. For an automobile in a repair shop or the like after occurrence of trouble, in order to investigate the cause of the trouble and which part is to be repaired, various checks such as a check of a control circuit, a harness check (including checks of lead wires and connectors) and the like are necessitated.

Further, according to Japanese Patent Application Laid-Open Nd. Sho 53-116896, a voltage applied to the A/F sensor is variably controlled in accordance with sensor current. In this apparatus, there will occur another malfunction. That is, sensor current exceeding a limit-current zone flows excessively when a positive or negative excessive voltage is applied to the sensor for some reason, thereby deteriorating the sensor operation.

SUMMARY OF THE INVENTION

It is therefore an object of the present invention to provide a malfunction detection apparatus and method.

It is another object of the present invention to discriminate trouble of a heater control system for use in a gas concentration sensor, which can accurately discriminate occurrence of trouble in a heater control system and specify the trouble part.

It is a further object of the present invention to suppress application of an excessive voltage to a gas concentration sensor.

In one aspect of the present invention, voltage across a heater for a gas concentration sensor is detected during both on-state and off-state of the heater and current flowing in the heater is detected in the on-state and off-state of the heater. Four such detected values are compared with respective predetermined thresholds to discriminates the presence or absence of trouble according to which one of the four values compared is different from a value in a normal state, and this specifies a part or location of the trouble.

In an other aspect of the present invention, whether a voltage to a gas concentration sensor is within a predetermined voltage zone is discriminated. Both terminals of the sensor are set to have the same potential when it is discriminated that the voltage applied to the sensor is out of the predetermined voltage zone. Alternatively, the voltage to be applied to the gas concentration sensor is calculated. When the calculated voltage is outside of a normal zone, the voltage to the sensor is restricted to a limit value.

BRIEF DESCRIPTION OF THE DRAWINGS

Other objects, features and advantages of the present invention will become more apparent from the following detailed description when read with reference to the accompanying drawings. In the accompanying drawings:

FIG. 15 is a table showing modes of various troubles and values of heater voltages and heater currents under a normal state and a trouble occurrence in the first embodiment;

DETAILED DESCRIPTION OF THE PREFERRED EMBODIMENTS

Figure 1:
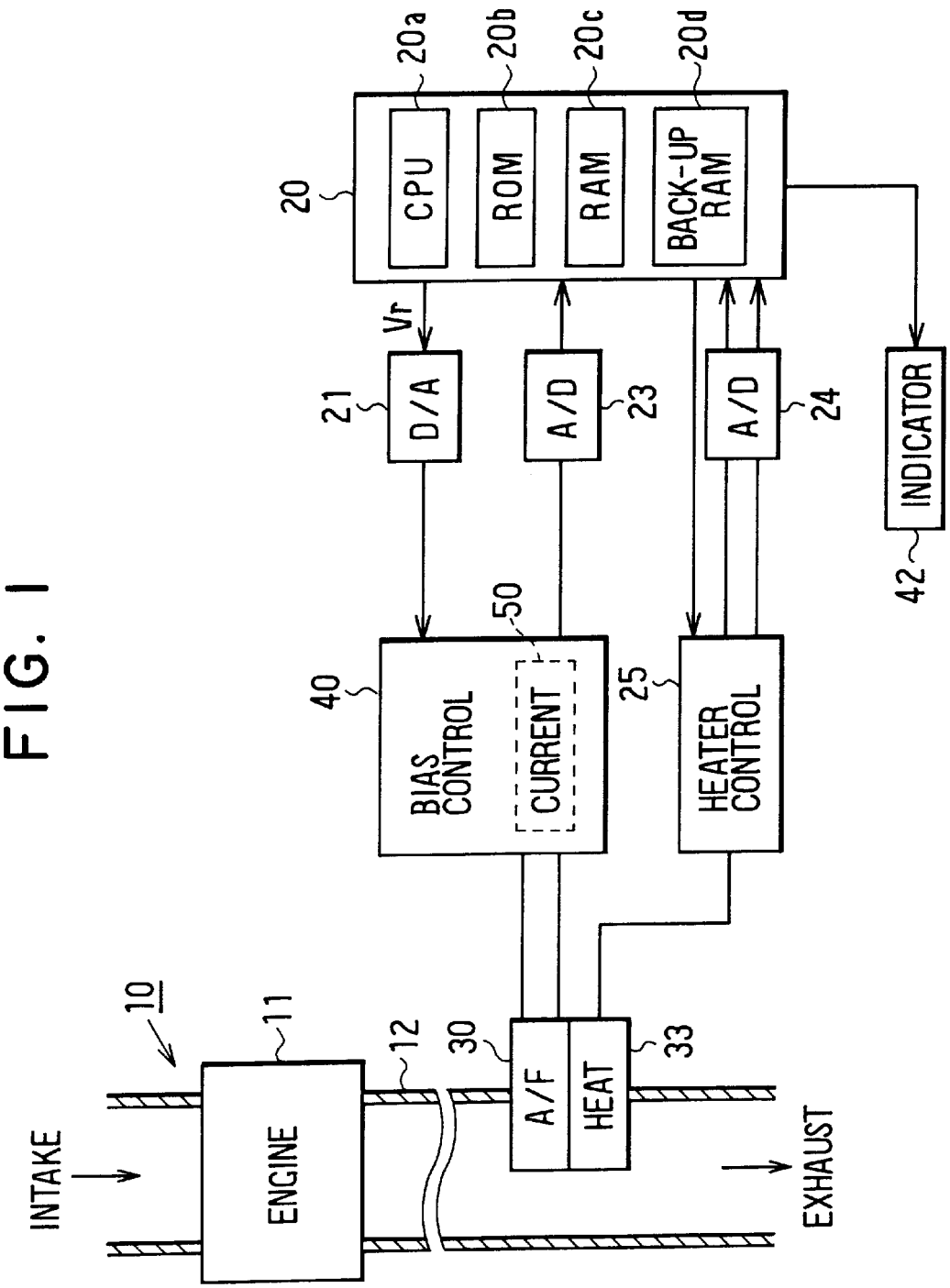
FIG. 1 is a block diagram showing an air-fuel ratio detection apparatus according to the first embodiment of the present invention.

The present invention will be described in detail hereinbelow with reference to various embodiments and modifications thereof shown in the drawings. It is to be noted that the following embodiments and modifications are directed to an oxygen concentration detection system which has a heater control and is applied to an electronically controlled gasoline injection engine mounted on a vehicle.

(First Embodiment)

In FIG. 1 showing a block diagram of an air-fuel ratio detecting apparatus, an oxygen responsive A/F (air-fuel ratio) sensor 30 of a limit-current type is used. The A/F sensor 30 having a heater 33 is attached to an exhaust pipe 12 extending from an engine body 11 of an engine 10 and outputs a linear air-fuel ratio detection signal (sensor current signal) proportional to the concentration of oxygen in the exhaust with application of a voltage instructed by a microcomputer 20. The microcomputer 20 is constructed by a CPU 20a for executing various kinds of processing, a ROM 20b, a RAM 20c, a back-up RAM 20d, and the like to control a heater control circuit 25 and a bias control circuit 40 in accordance with predetermined control programs. The back-up RAM 20d is constructed as a memory which can hold stored data even after turn-off of an electric power supply to the microcomputer 20.

A bias instruction signal Vr outputted from the microcomputer 20 is supplied to the bias control circuit 40 via a D/A converter 21. The output of the A/F sensor 30 corresponding to the air-fuel ratio (concentration of oxygen) is detected by a sensor current by a current detection circuit 50 in the bias control circuit 40. The detection value is inputted to the microcomputer 20 via an A/D converter 23. The microcomputer 20 controls ON/OFF of the heater 33 of the A/F sensor 30 by a predetermined control duty ratio signal. A heater voltage and a heater current according to the ON or OFF of the heater 33 are detected by the heater control circuit 25. Those detection values of heater voltage and heater current are inputted to the microcomputer 20 via an A/D converter 24. A malfunction indicator light 42 for indicating occurrence of a trouble (malfunction) in the heater control is connected to the microcomputer 20. The malfunction indicator light 42 is turned on or off in accordance with a discrimination result of a trouble discriminating process executed by the microcomputer 20.

Figure 2:
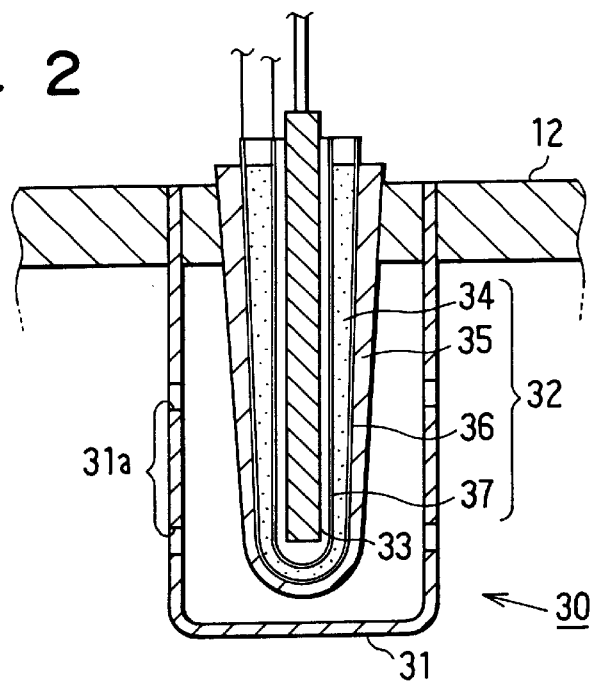
FIG. 2 is a cross sectional view showing an A/F sensor used in the first embodiment.

As shown in FIG. 2, the A/F sensor 30 is provided on the exhaust pipe 12, protruding toward the inside of the exhaust pipe 12. The sensor 30 is constructed by mainly a cover 31, a sensor body 32, and the heater 33. The cover 31 has a U-shape in cross section and a number of small holes 31a for communicating the inside and outside thereof. The sensor body 32 as a sensor element part generates a limit-current corresponding to the concentration of oxygen in a lean air-fuel ratio zone or the concentration of unburned gas (such as CO, HC, and $H_2$) in the rich air-fuel ratio zone.

In the sensor body 32, an exhaust-side electrode layer 36 is firmly attached to the external surface of a solid electrolyte layer 34 formed in a cup shape in cross section and an atmosphere-side electrode layer 37 is firmly attached to the internal surface of the solid electrolyte layer 34. On the outer side of the exhaust-side electrode layer 36, a diffusion resistance layer 35 is formed by a plasma spraying method or the like. The solid electrolyte layer 34 is made of an oxygen ion conducting oxide sintered body which is solid-solved in a material such as $ZrO_2$, $HfO_2$, $ThO_2$, and $Bi_2O_3$ with a material such as CaO, MgO, $Y_2O_3$, and $Yb_2O_3$ used as a stabilizer. The diffusion resistance layer 35 is made of a heat resisting inorganic material such as alumina, magnesia, silica, spinel and mullite. The exhaust-side electrode layer 36 and the atmosphere-side electrode layer 37 are both made of a noble metal with a high catalytic activity such as platinum and have the surfaces to which a porous chemical plating is performed. The area and the thickness of the exhaust-side electrode layer 36 is 10 to 100 $mm^2$ (square millimeters) and about 0.5 to 2.0 $\mu$m, respectively. On the other hand, the area and the thickness of the atmosphere-side electrode layer 36 are 10 $mm^2$ (square millimeters) or larger and about 0.5 to 2.0 $\mu$m.

The heater 33 is housed in the atmosphere-side electrode layer 37 to heat the sensor body 32 (the atmosphere-side electrode layer 37, the solid electrolyte layer 34, the exhaust-side electrode layer 36, and the diffusion resistance layer 35) by its heat generation energy. The heater 33 has a sufficient capacity of generating heat for activating the sensor body 32.

In the A/F sensor 30, the sensor body 32 generates a limit-current according to the concentration of oxygen in a zone leaner than the stoichiometric air-fuel ratio point. In this case, the limit-current corresponding to the concentration of oxygen is determined by the area of the exhaust-side electrode layer 36, and the thickness, the porosity and the average pore diameter of the diffusing resistance layer 35. The sensor body 32 is capable of detecting the concentration of oxygen in accordance with a linear characteristic thereof. Since a high temperature equal to or higher than about 600° C. is required for activating the sensor body 32 and the activating temperature range of the sensor body 32 is narrow, however, the sensor body temperature cannot be controlled in the active zone by heating with only exhaust gas of the engine 10. For this reason, in the present embodiment, the sensor body 32 is heated to the activation temperature zone by controlling the duty ratio of an electric power supply current to the heater 33. In a zone richer than the stoichiometric air-fuel ratio, the concentrations of unburned gases such as carbon monoxide (CO) change almost linearly with the air-fuel ratio and the sensor body 32 generates a limit-current according to the concentration of Co or the like.

Figure 3:
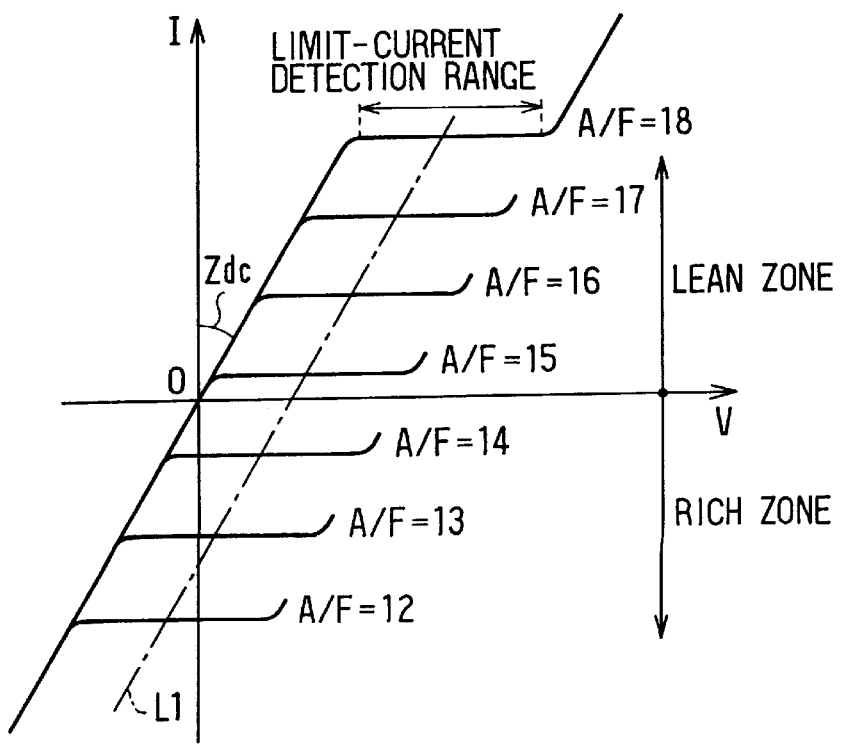
FIG. 3 is a V-I output characteristics of the A/F sensor shown in FIG. 2.

It will be understood from FIG. 3 showing the voltage-current characteristic (V-I characteristics) of the sensor body 32 that a current flowing to the solid electrolyte layer 34 of the sensor body 32, which is proportional to the A/F detected by the A/F sensor 30 and a voltage applied to the solid electrolyte layer 34 have a linear relation. In this case, straight line segments parallel to the voltage axis v constitute a limit-current detection zone which specifies the limit-current of the sensor body 32. Increases and decreases of the limit-current (sensor current) correspond to increases and decreases in the A/F (that is, lean and rich). Specifically, the more the A/F is shifted to the lean side, the more the limit-current increases to. The more the A/F is shifted to the rich side, the more the limit-current decreases to.

In the V-I characteristic, a voltage zone below the straight line segments (limit-current detection zone) parallel to the voltage axis v is a resistance-dominating zone. The gradient of the linear straight line segments in the resistance dominating zone is specified by the internal resistance (hereinbelow, referred to as an element impedance Zdc) of the solid electrolyte layer 34 in the sensor body 32. Since the element impedance Zdc changes with change in temperature, when the temperature of the sensor body 32 decreases, the gradient is reduced by the increase in Zdc.

Figure 4:
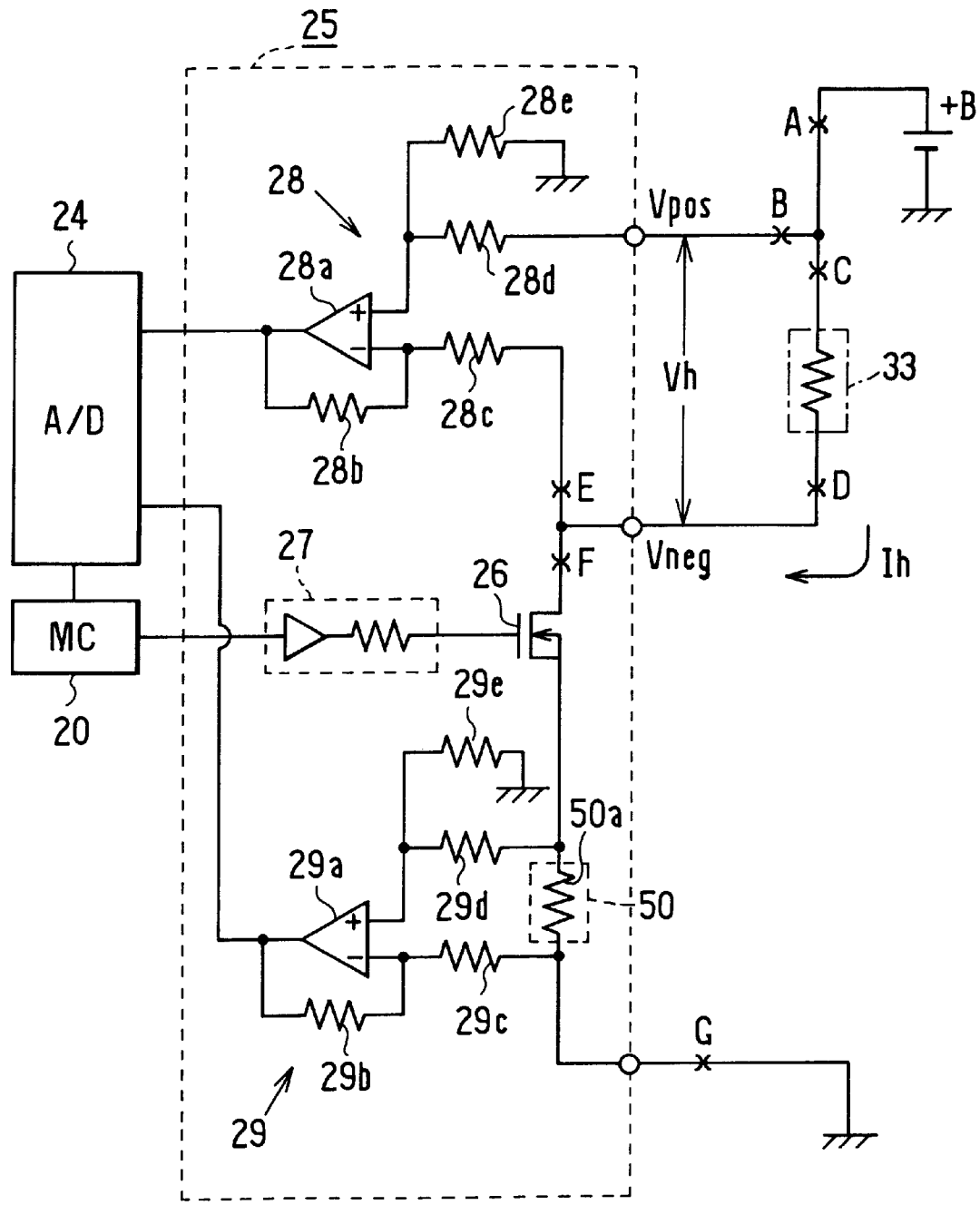
FIG. 4 is a circuit diagram showing a heater control circuit used in the first embodiment.

In the circuit diagram of FIG. 4 showing the heater control circuit 25, one end of the heater 33 is connected to a battery power source +B having the rated 12 volts and the other end is connected to the drain of an n-channel MOS transistor (MOS) 26 used as a semiconductor switching element. The gate of the MOS 26 is connected to the microcomputer 20 via a driver 27 and the source is connected to the ground via a resistor 50a of the current detection circuit 50 for heater current detection. In short, the MOS 26 is turned on or off in accordance with the control duty ratio signal of the microcomputer 20 and the turning-on operation of the heater 33 is controlled by the on/off operation of the MOS 26.

A heater voltage detection circuit 28 is constructed by a differential amplifying circuit having an operational amplifier 28a and resistors 28b to 28e, which measures the voltage across the heater 33 and outputs the result of the measurement to the microcomputer 20 via the A/D converter 24. A voltage Vh across the heater 33 corresponds to the difference between a voltage vpos on the battery side of the heater 33 and a voltage Vneg on the ground (GND) side (Vh=Vpos−Vneg). The value of resistance of the resistor 28b and that of the resistor 28e are equal (the values of resistances are R1) and the value of resistance of the resistor 28c and that of the resistor 28d are equal (the values of resistances are R2).

A heater current detection circuit 29 is constructed by a differential amplifying circuit having an operational amplifier 29a and resistors 29b to 29e, which converts a heater current Ih detected by the resistor 50a for heater current detection to a voltage signal and outputs the result to the microcomputer 20 via the A/D converter 24. The resistor 50a for heater current detection is set to have a small value so as not to cause influence on the heater current Ih, thereby assuring the performance of increasing the temperature of the heater 33.

When no trouble occurs in the heater control system in the on-state of the heater 33 (ON operation of the MOS 26) and in the off-state of the heater (OFF operation of the MOS 26), the heater control circuit 25 detects the voltage across the heater 33 and the heater current as follows. That is, in the on-state of the heater 33, a voltage applied across the heater 33 (heater on-voltage Von) becomes a value (value lower by an amount corresponding to a voltage drop of a resistance component of harness or the like) almost equal to a power source voltage VB of the heater 33. A current flowing in the heater 33 in that instance (heater on-current Ion) is substantially equal to a value obtained by dividing the power source voltage VB by a heater resistance value Rh. Specifically, when VB=12 volts, the heater on-voltage Von is equal to "about 11 volts" obtained from the equation;

Von=(R1/R2)·Vh

When Rh=2 ohms, the heater on-current Ion is obtained as "about 5 amperes" from the equation;

Ion=VB/Rh

That is, an output (output voltage of the operational amplifier 28a) of the heater voltage detection circuit 28 is equal to "about 11 volts" and a current conversion value of an output of the heater current detection circuit 29 (output voltage of the operational amplifier 29a) is equal to "about 5 amperes".

Since there is no potential difference across the heater 33 in the off-state of the heater, a voltage applied across the heater (heater off-voltage Voff) is "almost 0 volt". Since no potential difference of the resistor 50a for heater current detection occurs in this instance, an output voltage of the operational amplifier 29a becomes "almost 0 volt" and a current flowing to the heater 33 (heater off-current Ioff) is "0 ampere". That is, an output of the heater voltage detection circuit 28 (output voltage of the operational amplifier 28a) becomes "almost 0 volt" and a current conversion value of an output of the heater current detection circuit 29 (output voltage of the operational amplifier 29a) becomes "almost 0 ampere".

On the other hand, when any trouble occurs such as harness trouble (disconnection or opening of conductor or contact failure of a connector) in the heater control system, von, Ion, Voff, and Ioff as described above become values different from the respective normal values and the values are different according to the location (part) and the kind of trouble occurring. According to this embodiment, the trouble occurring-part and the contents (trouble mode) will be divided into the following (1) to (10). The result of analysis will be respectively described with reference to FIG. 15. In FIG. 15, the values of Von, Ion, Voff, and Ioff corresponding to each failure part and each failure mode are shown.

(1) Case of Opening of the A-part in FIG. 4

In the event of a trouble of "opening of the A-part" due to power supply line disconnection or the like, in the on-state of the heater 33 (ON operation of the MOS 26), the potentials on both ends of the heater 33 are both at the GND level and there is no potential difference between both ends of the heater 33. Consequently, the heater on-voltage Von is equal to "0 volt". Since an electric path connecting the battery power source +B, the heater 33, and GND is disconnected in this case, a current does not flow in the heater 33 and the heater on-current Ion becomes "0 ampere". In this case, the voltage level of Von and the current level of Ion are largely different from those in a normal state of the heater control system.

A non-inverting input terminal of the operational amplifier 28a is connected to GND via the resistor 28e and the operational amplifier 28a provides a negative feedback by the resistor 28b. Consequently, the inverting input terminal of the operational amplifier 28a becomes the GND level in the off-state of the heater 33 (OFF operation of the MOS 26) and an output voltage of the operational amplifier 28a becomes "0 volt" as the GND level. That is, the heater off-voltage Voff becomes "0 volt" in a manner similar to the normal state. The heater off-current Ioff becomes "0 ampere" in a manner similar to the normal state.

(2) Case of Opening of the B-part in FIG. 4

In the event of a trouble of "opening of the B-part" due to a line disconnection or the like, in the heater on-state (at the time of ON operation of the MOS 26), the non-inverting input terminal of the operational amplifier 28a is at the GND level and the heater on-voltage Von is equal to "0 volt". As obviously understood from the circuit diagram of FIG. 4 that even when the B-part is opened (disconnected), the heater current flows normally, so that the heater on-current Ion has the same value as that in the normal mode. The heater off-voltage Voff and the heater off-current Ioff in the off state of the heater (at the time of the OFF operation of the MOS 26) are values similar to those in the normal mode. That is, only the voltage level of Von is different and larger than a normal value, thereby enabling the trouble to be discriminated and the discrimination from the trouble of the A-part opening to be also realized.

(3) Case of Opening of the C-part in FIG. 4

In the event of the trouble of "the C-part opening" due to line disconnection or the like, in the heater on-state (at the time of the ON operation of the MOS 26), the non-inverting input terminal of the operational amplifier 28a has the potential of the heater power source voltage VB and its inverting input terminal has 0 volt. Specifically, the value of Von can be obtained from the equation:

$$Von=(R1/R2) \cdot VB$$

In this case, the heater on-voltage Von has a voltage value corresponding to the potential of the heater power source voltage VB, that is, is equal to "12 volts". When the C-part is opened, an electric path connecting the battery power source +B, the heater 33, and GND is disconnected. Even when the MOS 26 is ON, the heater current does not flow. Consequently, there is no voltage drop in harness or the like and the heater on-voltage Von has a potential higher than that in the normal state. The heater on-current Ion becomes "0 ampere" due to the disconnection of the electric path.

On the other hand, in the off-state of the heater (at the time of OFF operation of the MOS 26), the heater off-voltage Voff is obtained from the product of the power source voltage VB and a resistance voltage dividing value (R1/(R1+R2)). That is, the heater off-voltage Voff is obtained from the equation;

$$Voff=\{R1/(R1+R2)\} \cdot VB$$

and specifically becomes a value of about "9 volts". The heater off-current Ioff is equal to "0 ampere". In the case of the trouble of the C-part opening, the current level of Ion and the voltage level of Voff differ largely from the normal values, thereby enabling the trouble to be discriminated.

(4) Case of Opening of the D-part in FIG. 4

In the event of a trouble of the "D-part opening" due to line disconnection or the like, in a manner similar to the above-described case of the trouble of the C-part opening, Von=12 volts, Ion=0 ampere, Voff=9 volts, and Ioff=0 ampere. In a case where a trouble such that the heater 33 itself is damaged occurs, a similar detection result is shown.

(5) Case of Opening of the E-part in FIG. 4

In the event of a trouble of the "E-part opening" due to line disconnection or the like, when the heater is in the on-state (at the time of the ON operation of the MOS 26), the heater on-voltage Von is obtained from the equation;

$$Von=\{R1/(R1+R2)\} \cdot VB$$

Specifically, Von is a value of about "9 volts". Since the heater 33 is turned on when the E-part is opened, the heater on-current Ion can be normally detected (Ion=5 amperes).

On the other hand, in the off-state of the heater (at the time of the OFF operation of the MOS 26), in a manner similar to the heater on-voltage Von, the heater off-voltage Voff is obtained from the equation;

$$Voff=\{R1/(R1+R2)\} \cdot VB$$

Specifically, it is a value about "9 volts". The heater off-current Ioff is "0 ampere". In such a case of the E-part opening, the voltage level of Voff differs largely from the normal value, thereby enabling a trouble to be discriminated.

(6) Case of Opening of the F-part in FIG. 4

In the event of a trouble of the "F-part opening" due to line disconnection or the like, an electric path connecting the battery power source +B, the heater 33, the MOS 26, and GND is disconnected. Consequently, irrespective of the on-state or off-state of the heater 33 (ON or OFF of the MOS 26), the heater voltage and the current value are equal to those when the MOS 26 is OFF. That is, Von=0 volt, Ion=0 ampere, Voff=0 volt, and Ioff=0 ampere. In this case, the voltage level of Von and the current level of Ion are different largely from the normal values, thereby enabling a trouble to be discriminated.

(7) Case of Opening of the G-part in FIG. 4

In the event of a trouble of "opening of the G-part" due to line disconnection or the like as well, in a manner similar to the above case (6) of opening of the F-part, an electric path connecting the battery power source +B, the heater 33, the MOS 26, and GND is disconnected. Consequently, irrespective of the on-state or off-state of the heater 33 (ON or OFF of the MOS 26), the heater voltage and the current value are equal to those when the MOS 26 is OFF. That is, Von=0 volt, Ion=0 ampere, Voff=0 volt, and Ioff=0 ampere. In this case, the voltage level of Von and the current level of Ion differ largely from the normal values, thereby enabling a trouble to be discriminated.

(8) Case of Short-circuit Between D, E, F –GND in FIG. 4

In the event of a trouble of "short-circuit between D, E, F –GND", irrespective of the on-state or off-state of the heater 33 (ON or OFF of the MOS 26), the heater voltage is almost equal to the value when the MOS 26 is ON. In this case, however, there is no voltage drop of a resistance amount of harness or the like, a voltage equal to the power source voltage VB is applied to both ends of the heater. That is, Von=12 volts and Voff=12 volts. Since there is no potential difference between both ends of the resistor 50a for heater current detection, Ion=0 ampere and Ioff=0 ampere. In this case, the current level of Ion and the voltage level of Voff differ largely from the normal values, thereby enabling a trouble to be discriminated.

In a manner similar to the events of troubles of the opening of the C-part or the D-part, the current level of Ion and the voltage level of Voff differ largely from the normal values. When the voltage levels of Voff are compared, however, the trouble of the opening of the C-part or the D-part and the trouble of the short-circuit between D, E, F –GND can be distinguished. At the time of the opening of the C-part or the D-part, the value of Voff can be obtained by the product of the power source voltage VB and the resistance dividing value (R1/(R1+R2)). On the contrary, at the time of the short-circuit between the D, E, F –GND, the inverting input terminal of the operational amplifier 28a becomes at the GND level and an output of the operational amplifier 28a, that is, the Voff value can be obtained as "R1/R2×VB". Consequently, the voltage value of Voff in the event of the short-circuit between D, E, F –GND is higher than Voff in the event of the C-part opening or the D-part opening, so that when a threshold voltage for discriminating those Voff values is set, the opening of the C-part or the D-part and the short-circuit between D, E, F –GND can be distinguished.

(9) Case Where the MOS 26 is Continuously ON

In the event of a trouble that the "MOS 26 is continuously ON", irrespective of the on-state or off-state of the heater 33, the heater voltage and the current value are equal to values when the heater is turned on. That is, Von=11 volts, Ion=5 amperes, Voff=11 volts, and Ioff=5 amperes. In this case, the voltage level of Voff and the current level of Ioff differ largely from the normal values, thereby enabling occurrence of the trouble to be discriminated.

(10) Case Where the MOS 26 is Continuously OFF

In the event of a trouble where the "MOS 26 is continuously OFF", irrespective of the on-state or off-state of the heater 33, the heater voltage and the current values are equal to those when the heater is turned off. That is, Von=0 volt, Ion=0 ampere, Voff=0 volt, and Ioff=0 ampere. In this case, the voltage level of Von and the current level of Ion differ largely from the normal values, thereby enabling the occurrence of the trouble to be discriminated.

Figure 5:
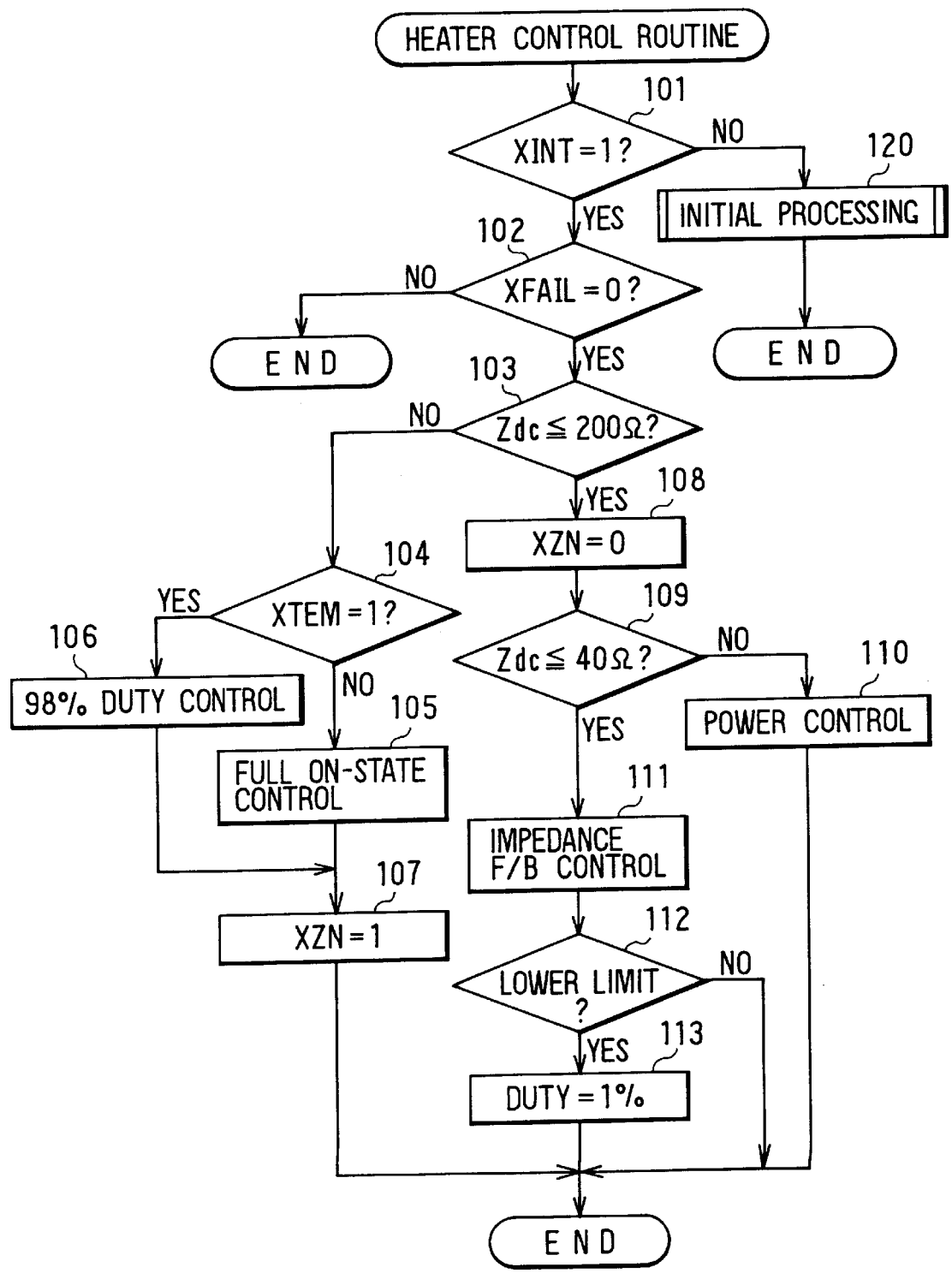
FIG. 5 is a flowchart showing a heater control routine executed in the first embodiment.
Figure 6:
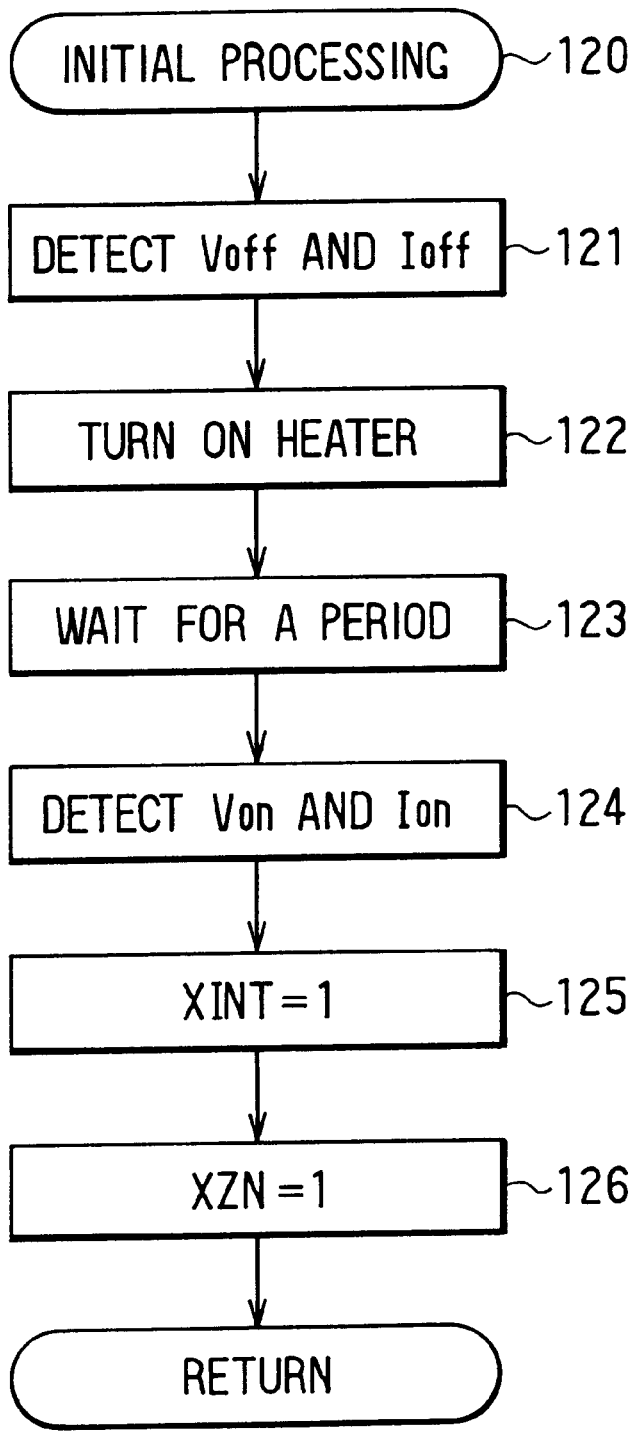
FIG. 6 is a flowchart showing an initial process routine in the heater control routine shown in FIG. 5.
Figure 7:
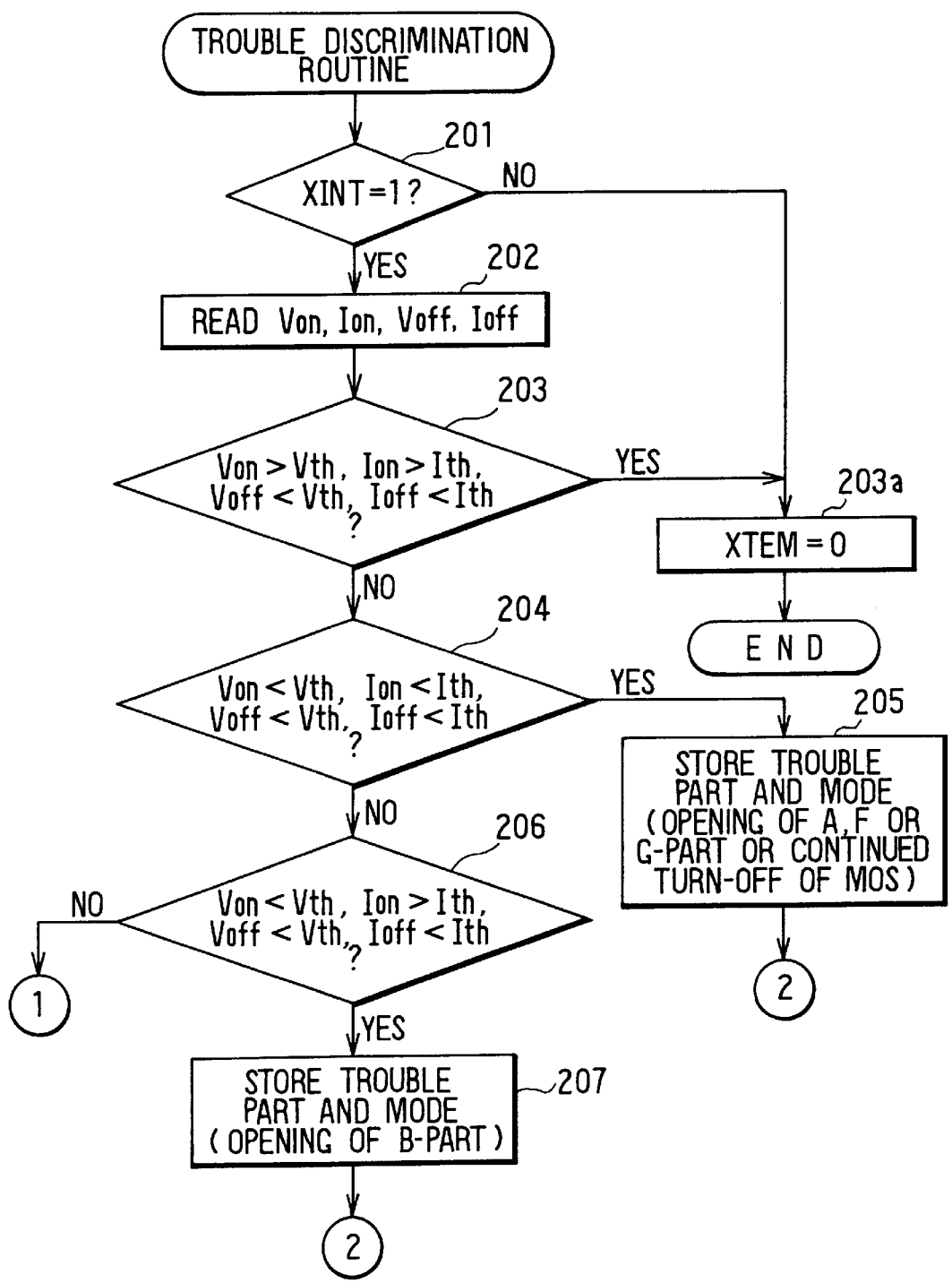
FIG. 7 is a flowchart showing a part of a routine for discriminating a trouble executed in the first embodiment.
Figure 8:
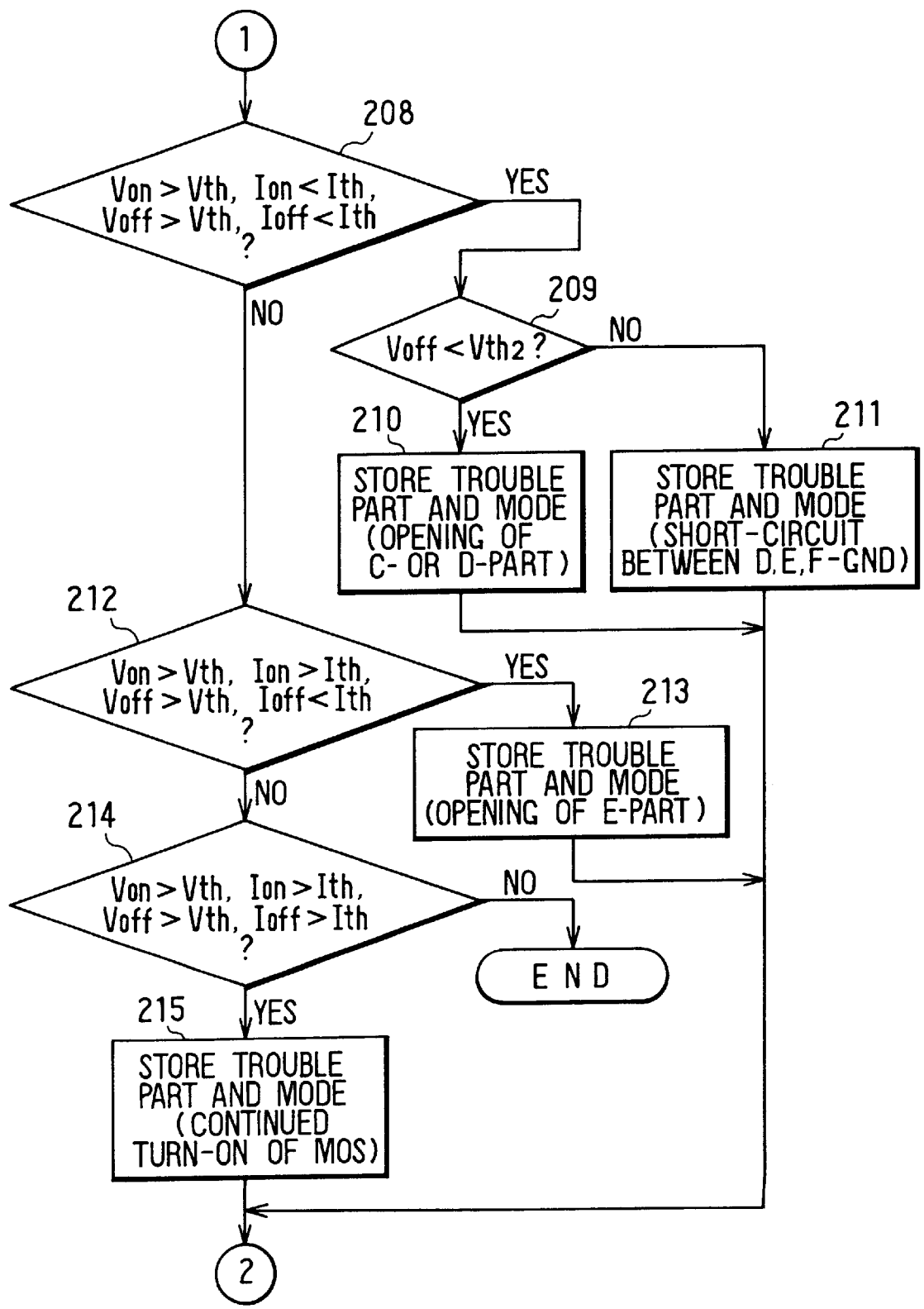
FIG. 8 is a flowchart, subsequent to FIG. 7, showing another part of the routine for discriminating the trouble.
Figure 9:
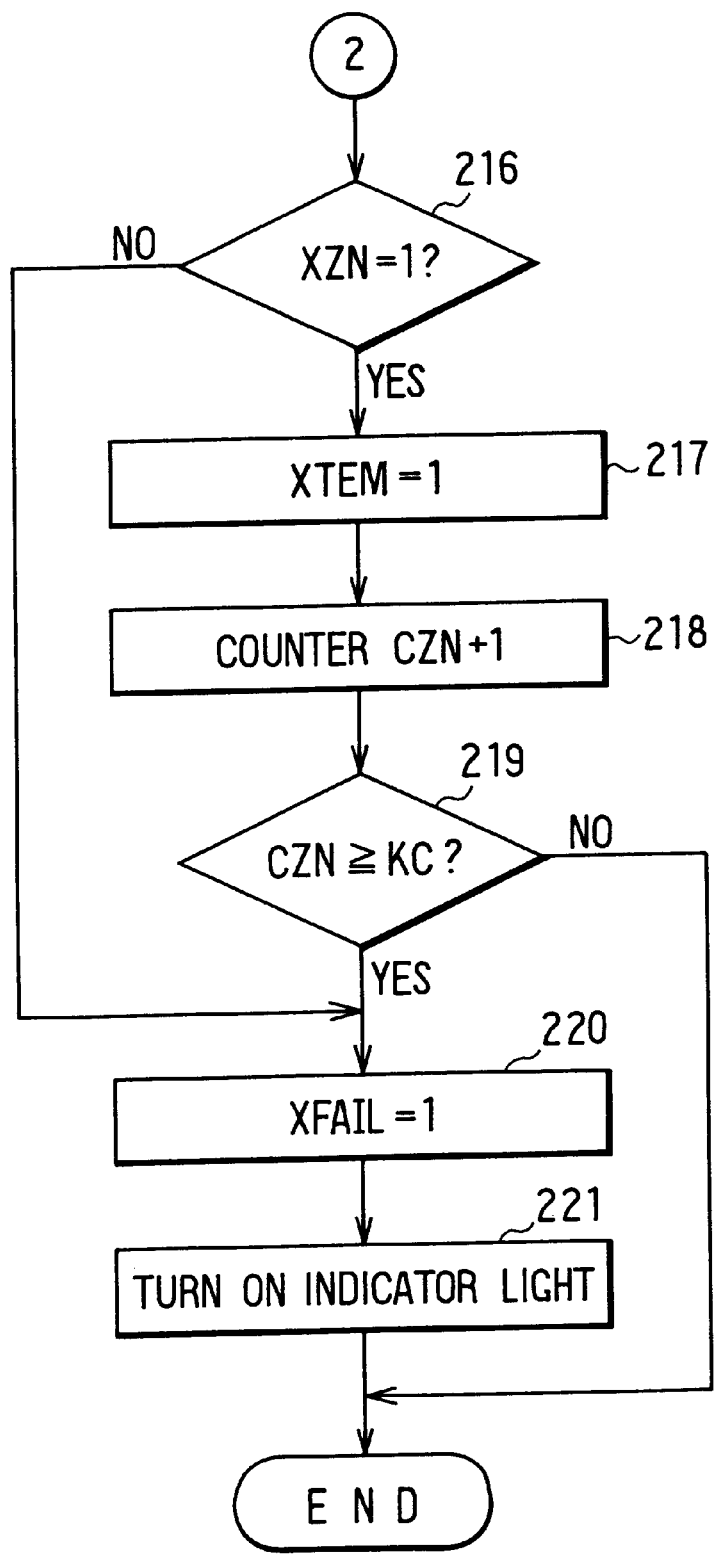
FIG. 9 is a flowchart, subsequent to FIGS. 7 and 8, showing the other part of the routine for discriminating the trouble.

The microcomputer 20 is programmed to control the heater 33 and detect the above malfunctions in the heater control system by execution of control routines shown in FIGS. 5 to 9. Each of the routines of FIG. 5 and FIGS. 7 to 9 is activated by a timer interruption at predetermined intervals (for example, 128 msec period) by the CPU 20a. The routines of FIGS. 7 to 9 are executed just after the routine of FIG. 5.

In the heater control routine of FIG. 5, the CPU 20a discriminates whether an initial flag XINT is "0" or not in step 101. The initial flag XINT indicates whether an initial processing required at the time of ON operation of an ignition (IG) key is performed or not. "XINT=0" indicates that the initial processing has not been performed. "XINT=1" indicates that the initial processing has been performed. In case of XINT=0, the CPU 20a advances to step 120, executes the initial processing shown in FIG. 6, and after that, finishes the routine.

In this initial processing routine, the heater off-voltage Voff and the heater off-current Ioff are detected before the turn-on control of the heater 33 is started and, after that, the heater 33 is turned on (ON) and the voltage value and the current value when the heater is ON are detected. Specifically, first in step 121, the CPU 20a detects the heater off-voltage Voff and the heater off-current Ioff on the basis of output values of the heater voltage detection circuit 28 and the heater current detection circuit 29. The CPU 20a turns on the heater 33 in following step 122 and waits in such a state only for a predetermined time (step 123). The waiting time is a time required until the voltage and the current values converge after the turn-on of the heater 33. Specifically, about 200 msec is sufficient.

After waiting for the predetermined time, the CPU 20a detects the heater on-voltage Von and the heater on-current Ion in step 124 and sets "1" in the initial flag XINT in the following step 125. Further after that, the CPU 20a sets "1" in a full on-state flag XZN in step 126 and returns to the routine of FIG. 5. The full on-state flag XZN is a flag indicating whether a full on-state control will be performed or not. "XZN=1" shows that the full on-state control is performed and "XZN=0" shows that the full on-state control is not performed.

On the other hand, when the initial flag XINT is set in the initial process routine, step 101 in FIG. 5 is discriminated affirmatively each time after that. The CPU 20a discriminates whether a trouble occurrence flag XFAIL is "0" or not in step 102. The trouble occurrence flag XFAIL shows a discrimination result of the presence or absence of a trouble in the heater control system. "XFAIL=0" shows the presence of the trouble in the heater control system and "XFAIL=1" indicates that there is no trouble in the heater control system. The flag XFAIL is determined in a trouble discrimination routine of FIGS. 7 to 9. If the trouble occurrence flag XFAIL is "1", the CPU 20a finishes the main routine as it is. That is, the on-state control of the heater 33 is not executed.

Figure 10:
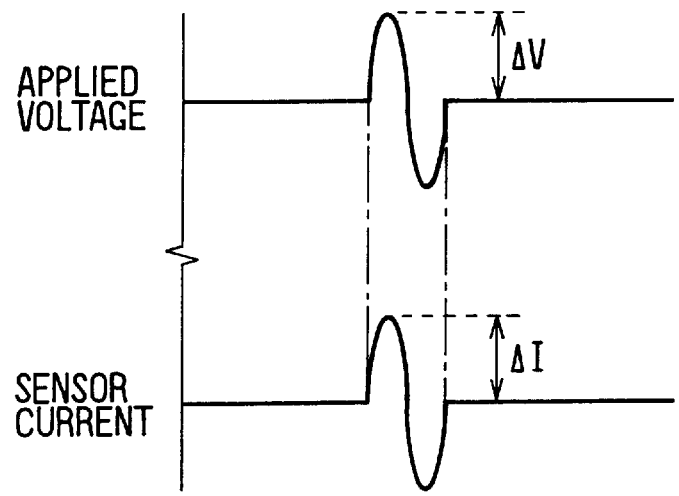
FIG. 10 is a waveform chart for explaining a method of detecting an element impedance in the first embodiment.

If the trouble occurrence flag XFAIL is "0", the CPU 20a advances to step 103 and discriminates whether the sensor element impedance Zdc is a predetermined discrimination value (about 200 ohms in the embodiment) or lower for discriminating a half- or semi-active state of the sensor body 32. The element impedance Zdc is detected as follows. That is, in case of detecting the element impedance Zdc, as shown in FIG. 10, a voltage applied to the A/F sensor 30 is temporarily changed to the positive direction and the negative direction. The element impedance Zdc is calculated from a voltage change amount $\Delta V$ and a current change amount LI of either the positive or negative direction at the time of the voltage change ($Zdc=\Delta V/\Delta I$). The element impedance Zdc may alternatively be detected on the basis of change amounts of the voltage and the current on both of the positive and negative sides and the element impedance Zdc may further alternatively be detected from the sensor current Ineg when the negative voltage Vneg is applied ($Zdc=Vneg/Ineg$).

For example, when the element temperature is low such as a low temperature start of the engine 10, Zdc>200 ohms and the CPU 20a advances to step 104 and discriminates whether a temporary trouble flag XTEM is "1" or not. "1" is set to the temporary trouble flag XTEM when the occurrence of a trouble in the heater control system is temporarily discriminated at the time of the start of the engine. The operation is executed by a trouble discriminating routine.

In case of "XTEM=0", that is, when the trouble occurrence is not temporarily discriminated at the time of the engine start, the CPU 20a advances to step 105 and executes the "full on-state control" of the heater 33. In the full on-state control, the control duty ratio signal to the heater 33 is maintained at 100% and a promotion of activating the sensor is preferentially executed.

On the other hand, when "XTEM=1", that is, when the trouble occurrence is temporarily discriminated at the time of the engine start, the CPU 20a advances to step 106 and executes a "98% duty control" of the heater 33. In the 98% duty control, OFF time of Duty=about 2% is set so that the heater off-voltage Voff and the heater off-current Ioff can be continuously detected when the trouble occurrence is temporarily discriminated. By detecting Voff and Ioff, the trouble discrimination by the trouble discriminating routine which will be described hereinlater can be performed. After that, the CPU 20a sets "1" in the full on-state flag XZN in step 107 and finishes the routine.

After the turn-on of the heater is started, the element temperature rises by heating operation of the heater 33 or the element temperature is high from the beginning. When step 103 is affirmatively discriminated, the CPU 20a advances to step 108 and clears the full on-state flag XZN to "0". The CPU 20a discriminates whether the element impedance Zdc is equal to or lower than a predetermined discrimination value (about 40 ohms in the embodiment) for starting an element impedance feedback (F/B) control. The discrimination value in step 109 is used to discriminate an activation state of the sensor body 32 and is set to a value which is a target impedance (30 ohms in the embodiment) "+ about 10 ohms".

Figure 11:
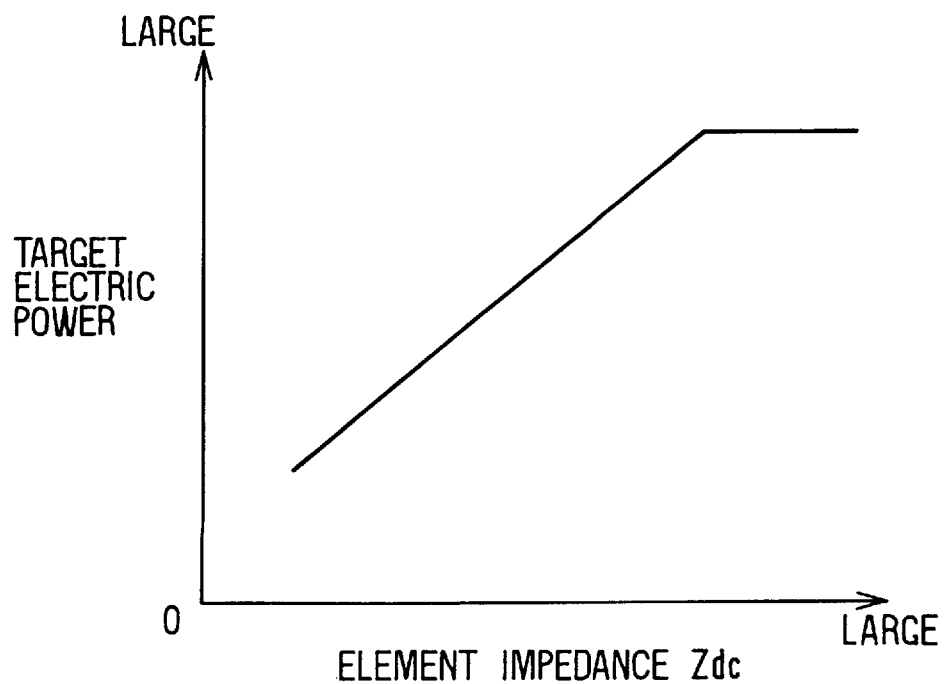
FIG. 11 is a data map showing a relation between the element impedance and a target electric power supplied to the heater in the first embodiment.

When step 109 is negatively discriminated before completion of the activation of the A/F sensor 30, the CPU 20a advances to step 110 and controls the turn-on of the heater 33 by "electric power control". In this instance, as shown in a map of FIG. 11, a target electric power is determined according to the element impedance Zdc and a control duty ratio for turning on the heater 33 is calculated according to the target electric power value.

On the other hand, when step 109 is affirmatively discriminated after completion of the activation of the A/F sensor 30, the CPU 20a executes an "element impedance F/B control" in step 111. In the element impedance F/B control, the duty ratio Duty for turning on the heater 33 is calculated in the following procedure. In the embodiment, a PID control procedure is used as an example.

That is, first, a proportional term GP, an integral term GI, and a derivative term GD are calculated by the following equations (1) to (3).

$$GP=KP \cdot (Zdc-ZdcTG) \quad (1)$$

$$GI=GIi-1+KI \cdot (Zdc-ZdcTG) \quad (2)$$

$$GD=KD \cdot (Zdc-Zdci-1) \quad (3)$$

In the equations, "KP" denotes a proportional constant, "KI" is an integral constant, and "KD" is an integral constant, and a suffix "i−1" shows a value of a previous process.

By adding the proportional term GP, the integral term GI, and the derivative term GD, the duty ratio Duty for turning on the heater is calculated (Duty=GP+GI+GD). The heater control procedure is not limited to the PID control but a PI control or a P control may be executed.

After that, the CPU 20a discriminates whether the duty ratio Duty set by the element impedance F/B control is larger than a predetermined lower limit guard value or not in step 112. The lower limit guard of the duty ratio Duty is used to limit Duty so as not to be "0%" even when an exhaust temperature is high and the turn-on of the heater 33 is unnecessary at the time of high load operation or the like. Specifically, it is sufficient to set the lower limit guard value to about "1%". By turning on the heater 33 with a small duty even when the turn-on of the heater 33 is unnecessary, the heater on-voltage Von and the heater on-current Ion can be detected under any operating state and the trouble discrimination by the trouble discriminating routine which will be described hereinlater can be performed.

When the duty ratio Duty is lower than the lower limit guard value, the CPU 20a limits the duty ratio Duty with the lower limit guard value (1%) in step 113 and, after that, finishes this routine. When the duty ratio Duty is higher than the lower limit guard, the CPU 20a finishes the routine as it is.

The process for discriminating a trouble in the heater control system will be described with reference to a flowchart of FIGS. 7 to 9. Although various troubles of the heater control system shown in FIG. 15 are discriminated on the basis of the heater on-voltage Von, the heater on-current Ion, the heater off-voltage Voff, and the heater off-current Ioff in the trouble discriminating process of the embodiment, those Von, Ion, Voff, and Ioff are basically detected synchronously with the rise of "OFF→ON" of the turn-on control signal of the heater 33. Only at the time of the ON operation of the IG key, however, Von, Ion, Voff, and Ioff are detected in accordance with the above initial processing of FIG. 6.

Figure 12:
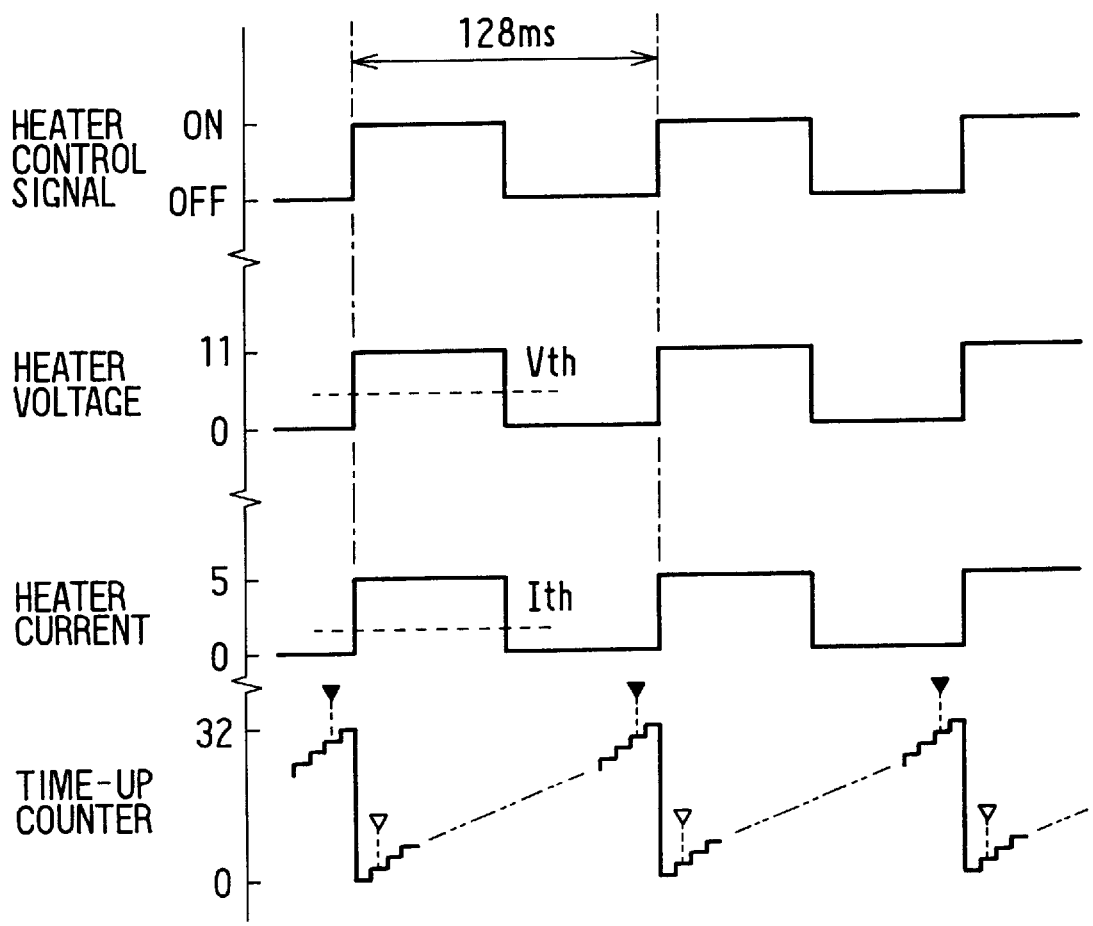
FIG. 12 is a time chart showing a heater operation in the first embodiment.

As shown in FIG. 12, timings of detecting Von, Ion, Voff, and Ioff are determined corresponding to the turn-on control signal of the heater 33. A time-up counter is counted up with a cycle of 4 msec and the count value changes in a range from "0" to "32". A timing when the time-up counter is cleared to "0" and a timing of the rise of the turn-on control signal of the heater 33 are synchronized. The heater off-voltage Voff and the heater off-current Ioff are detected just before the count value of the time-up counter is cleared to "0", that is, when the count value=31 (timing ▼ in the chart of FIG. 12). The heater on-voltage Von and the heater on-current Ion are detected just after the count value is cleared to "0", that is, when the count value=1 (timing ▽ in the chart of FIG. 12). The detection values of Von, Ion, Voff, and Ioff are continuously stored and held in the RAM 20c in the microcomputer 20.

"Vth" in the chart shows a threshold voltage for discriminating whether a voltage is the on-voltage Von or the off-voltage Voff of the heater 33 and "Ith" is a threshold current for discriminating whether a current is the on-current Ion and the off-current Ioff of the heater 33. Those threshold values Vth and Ith are preliminarily set. Specifically, it is set that Vth=5 volts and Ith=1.5 amperes.

Referring to FIGS. 7 to 9, when the routine for discriminating a trouble in the heater control system is started, first, the CPU 20a discriminates whether the initial flag XINT is "1" or not in step 201 in FIG. 7. Under the condition of XINT=1, the CPU 20a reads the latest values of Von, Ion, Voff, and Ioff in the RAM 20c in step 202.

After that, the CPU 20a discriminates whether normal conditions of the heater control system are satisfied or not from the read values Von, Ion, Voff, and Ioff and the predetermined thresholds Vth and Ith in step 203. In the step, whether all of the following four conditions are satisfied or not is discriminated. That is, it is discriminated whether all of the following relations are satisfied:

Von>Vth,

Ion>Ith,

Voff<Vth, and

Ioff<Ith.

In this case, if the heater control system is normal, all of the above four conditions are satisfied (FIG. 15). After clearing the temporary trouble flag XTEM to "0" in step 203a, the CPU 20a finishes the routine.

On the other hand, when the conditions in step 203 are not satisfied, the CPU 20a advances to step 204 and discriminates whether all of the following four conditions are satisfied or not. That is, it is discriminated whether all of the following relations are satisfied:

Von<Vth,

Ion<Ith,

Voff<Vth, and

Ioff<Ith.

In this case, if a trouble such as the opening of the A-part, the F-part, or the G-part in FIG. 4 or that the MOS 26 is continuously OFF occurs, step 204 is discriminates affirmatively. That is, as shown in FIG. 15, when the trouble such that the A-part, the F-part, or the G-part is open or the MOS 26 is continuously OFF occurs, although the values of Voff and Ioff are normal values, the values of Von and Ion are smaller than the normal values and are below the threshold values Vth and Ith (Von=0 volt and Ion=0 ampere). When step 204 discriminates affirmatively, the CPU 20a stores a trouble E-part and a trouble mode (the trouble information of the opening of the A-part, the F-part or the G-part or that the MOS 26 is continuously OFF) at that time in the back-up RAM 20d in step 205.

When the conditions of step 204 are not satisfied, the CPU 20a advances to step 206 and discriminates whether all of the following four conditions are satisfied or not. That is, whether all of the following relations are satisfied:

Von<Vth,

Ion>Ith,

Voff<Vth, and

Ioff<Ith.

In this case, when a trouble such as the opening of the B-part in FIG. 4 occurs, step 206 is discriminated affirmatively. That is, as shown in FIG. 15, although the values of Ion, Voff, and Ioff are normal values when the trouble of the opening of the B-part occurs, only the value of Von is smaller than the normal value and is below the threshold Vth (Von=0 volt). In the case where the step 206 is affirmatively discriminated, the CPU 20a stores the trouble D-part and the mode (trouble information of the opening of the B-part) at that time in the back-up RAM 20d in step 207.

When the conditions of the step 206 are not satisfied, the CPU 20a advances to step 208 in FIG. 8 and discriminates whether all of the following four conditions are satisfied or not. That is, it is discriminated whether all of the following relations are satisfied:

Von>Vth,

Ion<Ith,

Voff>Vth, and

Ioff<Ith.

In this case, if a trouble such as the opening of the C-part or the D-part of FIG. 4 or short-circuit between D, E, F –GND occurs, the step 208 is discriminated affirmatively. That is, as shown in FIG. 15, when the trouble such as the opening of the C-part or the D-part or the short-circuit between D, E, F –GND occurs, the values of Von and Ioff are normal values (Von is 12 volts which is almost a normal value). On the contrary, the value of Ion is smaller than the normal value and is below the threshold value Ith (Ion=0 ampere). The value of Voff is larger than the normal value and exceeds the threshold Vth (Voff=9 volts or 12 volts).

When step 208 affirmatively discriminates, the CPU 20a distinguishes if the trouble at that time is due to the opening of the C-part or the D-part or the short-circuit between D, E, F –GND in step 209. Specifically, when the trouble such as the opening of the C-part or the D-part or the short-circuit between D, E, F –GND occurs, although the value of Voff exeeds the threshold vth (=5 volts) in any case, the value of voff when the C-part or the D-part is opened is lower than the value of voff in the case of the short-circuit between D, E, F –GND as described above. Voff in the former case is about 9 volts and Voff in the latter case is about 12 volts. A second threshold voltage Vth2 is set between the values (Vth2=about 10.5 volts) and a comparison between the threshold voltage Vth2 and Voff is performed.

That is, the CPU 20a discriminates whether Voff<Vth2 is satisfied or not in step 209. If voff<Vth2, the CPU 20a advances to step 210, regards that the trouble due to the opening of the C-part or the D-part occurs, and stores the trouble information into the back-up RM 20d. If Voff≧Vth2, the CPU 20a advances to step 2 11, regards that the trouble due to the short-circuit between D, E, F –GND occurs, and stores the trouble information into the back-up RAM 20d.

On the other hand, when the conditions of the step 208 are not satisfied, the CPU 20a advances to step 212 and discriminates whether all of the following four conditions are satisfied or not. That is, it is discriminated whether all of the following relations are satisfied:

Von>Vth,

Ion>Ith,

Voff>Vth, and

Ioff<Ith.

In this case, if the trouble such as the opening of the E-part of FIG. 4 occurs, the step 212 affirmatively discriminates. That is, as shown in FIG. 15, when the trouble such as the opening of the E-part occurs, although the values of Von, Ion, and Ioff are normal values (Von is 9 volts which is almost a normal value), only the value of Voff is larger than the normal value and exceeds the threshold Vth (Voff=9 volts). When the step 212 affirmatively discriminates, the CPU 20a stores the troubled location and the mode (trouble information of the opening of the E-part) at that time in the back-up RAM 20d in step 213.

When the conditions of the step 212 are not satisfied, the CPU 20a advances to step 214 and discriminates whether all of the following four conditions are satisfied or not. That is, it is discriminated whether all of the following relations are satisfied:

Von>Vth,

Ion>Ith,

Voff>Vth, and

Ioff>Ith.

In this case, if the trouble such that the MOS 26 of FIG. 4 is continuously ON occurs, the step 214 affirmatively discriminates. That is, as shown in FIG. 15, when the trouble that the MOS 26 is continuously ON occurs, although the values of Von and Ion are normal values, the values of Voff and Ioff are larger than the normal values and exceed the thresholds Vth and Ith (Voff=11 volts and Ioff=5 amperes). When the step 214 affirmatively discriminates, the CPU 20a stores the troubled location and the mode (the trouble information that the MOS 26 is continuously ON) at that time in the back-up RAM 20d in step 215. If the conditions of the step 214 are not satisfied, the CPU 20a finishes the routine.

After the series of the trouble discrimination, when the trouble occurrence is discriminated (after the processing of steps 205, 207, 210, 211, 213 and 215), the CPU 20a executes the processes of steps 216 to 220 of FIG. 9. Specifically, the CPU 20a discriminates whether the full on-state flag XZN is "1" or not, that is, whether the full on-state control of the heater 33 (or the 98% Duty control) is performed or not in step 216. When XZN=0 and the electric power control of the heater 33 or the element impedance F/B control is performed, the CPU 20a negatively discriminates the step 216 and immediately advances to the step 220. The CPU 20a sets "1" in the trouble occurrence flag XFAIL in the step 220, turns on the malfunction indicator light 42 in the following step 221, and after that, finishes the routine. By the turn-on of the malfunction indicator light 42, the occurrence of the trouble is warned to the occupant of the vehicle.

On the other hand, when XZN=1 and the full turn-on control of the heater 33 (or the 98% duty control) is performed, the CPU 20a discriminates the step 216 affirmatively, advances to step 217 and sets "1" in the temporary trouble flag XTEM. After that, the CPU 20a increments the counter CZN by "1" in step 218 and discriminates whether the counter CZN is equal to or larger than a predetermined discrimination value KC in the following step 219. The discrimination value KC denotes a time necessary to determine the occurrence of the trouble and is a count value corresponding to about "three seconds" in the embodiment.

In case of CZN<KC, the CPU 20a finishes the routine as it is. In case of CZN≧KC, the CPU 20a advances to step 220. The CPU 20a sets "1" in the trouble occurrence flag XFAIL in the step 220 and turns on the malfunction indicator light 42 in the following step 221, and after that, finishes the routine.

When the trouble is not discriminated in the beginning of the start of turn-on of the heater 33 in the trouble discriminating routine of FIGS. 7 to 9 and the full turn-on control is performed, Voff and Ioff cannot be detected. Consequently, in such a case, the full turn-on control is finished and the trouble discriminating processing is temporarily interrupted until the electric power control or the element impedance F/B control is started (even during the full turn-on control, if Voff and Ioff can be detected, the trouble discrimination can be performed).

Figure 13:
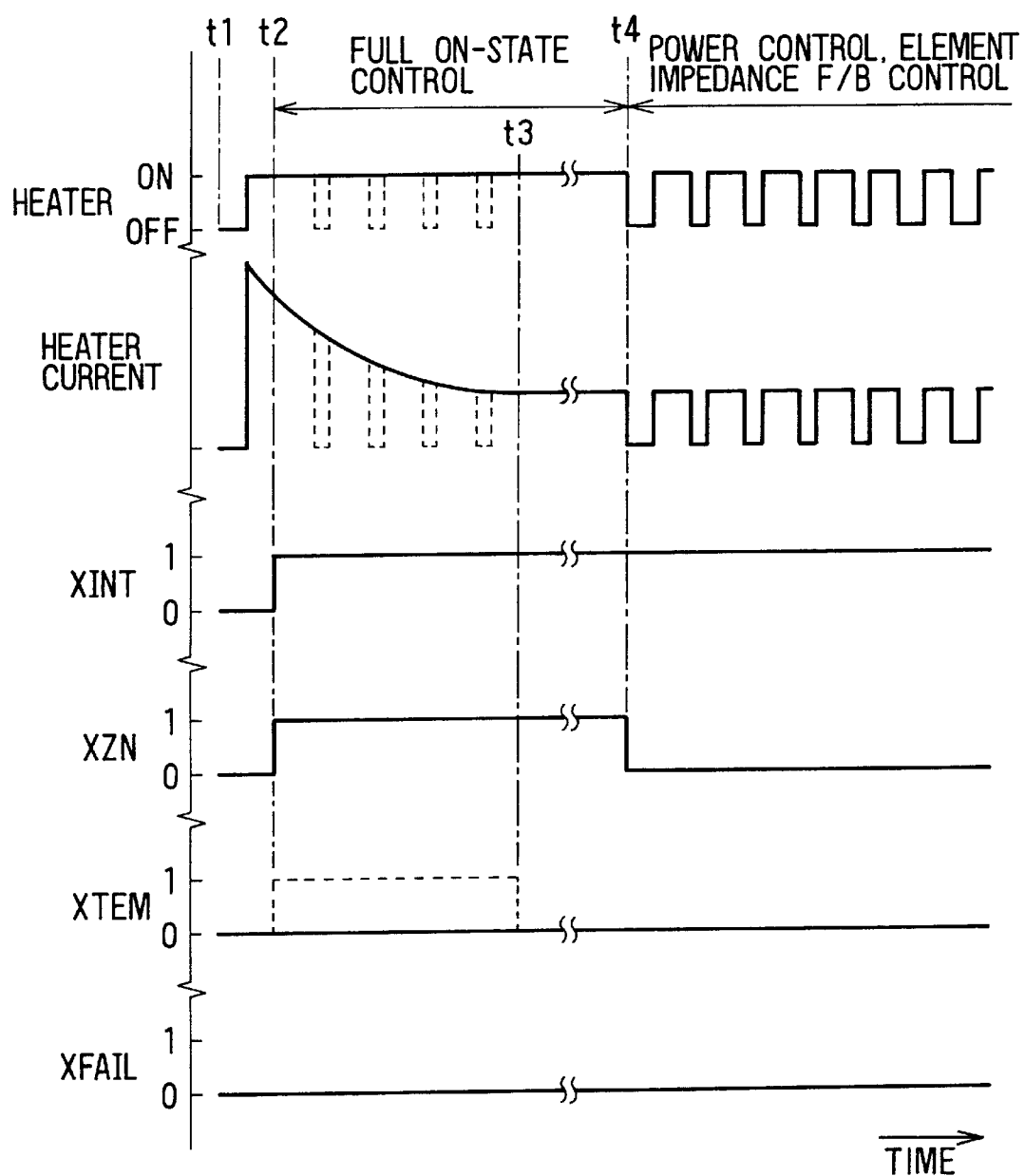
FIG. 13 is a time chart showing a heater control operation in the first embodiment when the engine is started.
Figure 14:
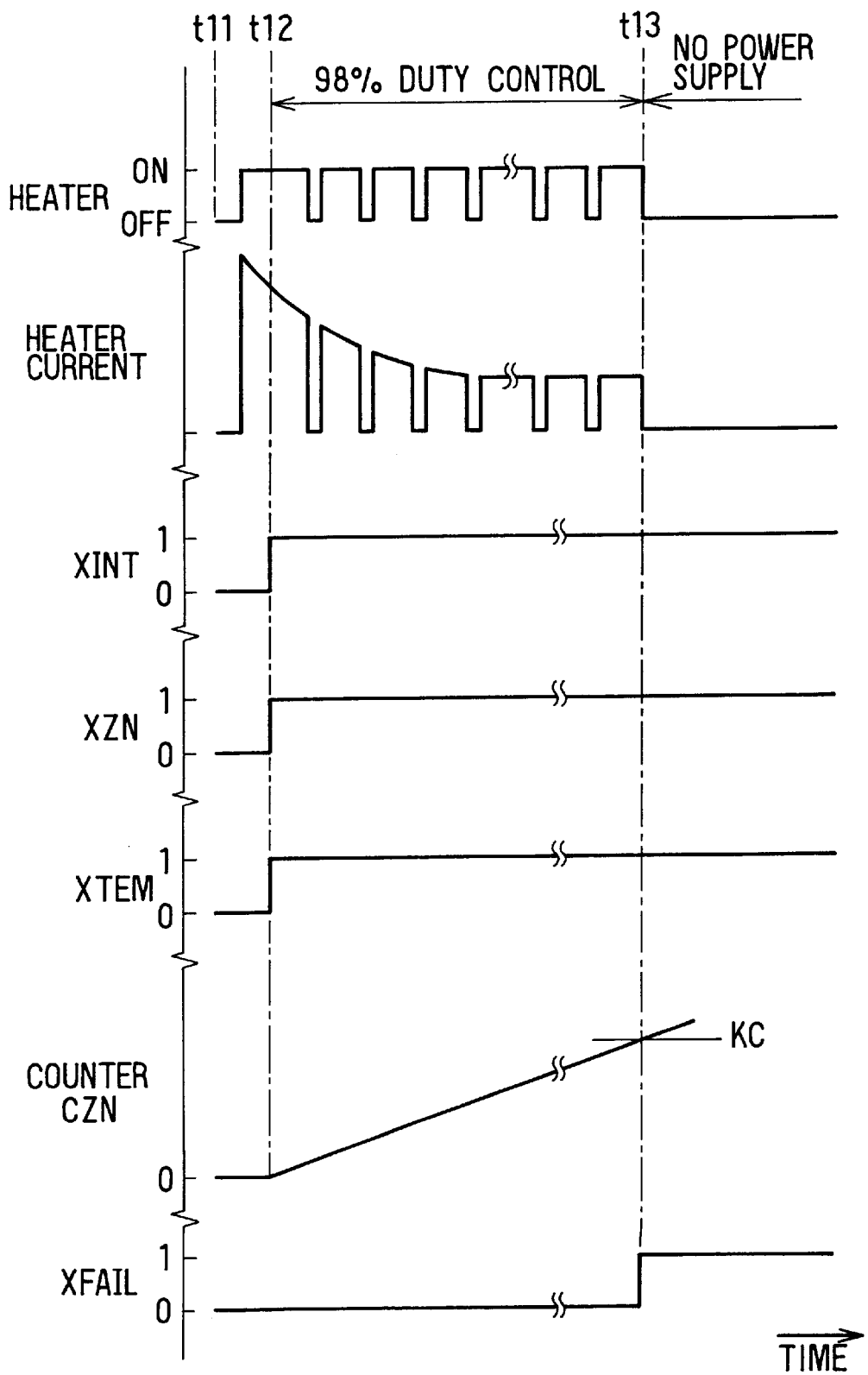
FIG. 14 is a time chart showing a heater control operation in the first embodiment when the engine is started.

The operation for controlling the turn-on of the heater 33 at the time of a low temperature start of the engine 10, change in the heater current, and operating states of various flags are shown in FIGS. 13 and 14. More specifically, FIG. 13 shows a case where no trouble occurs in the heater control system while FIG. 14 shows a case where a trouble occurs.

In FIG. 13, the power source of the microcomputer 20 is turned on at a time t1 and the initial processing of FIG. 6 is performed in a period from the time t1 to t2. In this case, after the heater off-voltage Voff and the heater off-current Ioff are detected, the heater on-voltage Von and the heater on-current Ion are detected. The trouble is discriminated by using the first values of Voff, Ioff, Von and Ion (FIGS. 7 to 9). Although the heater current is relatively large since the heater resistance is small in the beginning of the start of the turn-on of the heater, the heater current is converged to the normal value (5 amperes) with warming up.

At the time t2, "1" is set to the initial flag XINT and "1" is set to the full turn-on flag XZN. After that, the full turn-on control of the heater 33 is performed in a period from the time t2 to t4. That is, the control duty ratio Duty of the on-state of the heater is maintained at 100%. Although the time required for the full turn-on control is different in accordance with the degree of a cold state of the A/F sensor 30, it is a time of about 7 seconds at longest. The full turn-on flag XZN is cleared to "0" at the time t4 and the electric power control of the heater 33 and the element impedance F/B control are performed after that (FIG. 5).

When the occurrence of the trouble is temporarily discriminated by Von, Ion, Voff, and Ioff detected in the initial process in FIG. 13, the "98% Duty control" in which "1" is set to the temporary trouble flag XTEM as shown by a broken line in the diagram and 2% of the duty ratio Duty is set to OFF time is performed at the time t2 (YES in step 104 in FIG. 5). In this case, if the discrimination of the trouble occurrence is temporary, the temporary trouble flag XTEM is reset to "0" at the time t3 in the diagram (step 203*a* in FIG. 7) and the turn-on of the heater is switched from the 98% duty control to the full turn-on control (NO in step 104 in FIG. 5).

On the other hand, in FIG. 14, either one of the various troubles shown in FIG. 15 occurs from the beginning of the start of the turn-on. In this case, the trouble discrimination is performed by using the values of Von, Ion, Voff, and Ioff detected in the initial processing from the time t11 to t12 and the occurrence of the trouble is temporarily discriminated. The temporary trouble flag XTEM or the like is set at time t12 and the count up of the counter CZN is started.

After the time t12, if the trouble occurrence is not cancelled during the execution of the 98% duty control, "1" is set to the trouble occurrence flag XFAIL at time t13 when the value of the counter CZN reaches a predetermined discrimination value KC. In this case, the trouble information such as the trouble location and the trouble mode is stored in the back-up RAM 20*d* and the malfunction indicator light 42 is turned on. The on-state of the heater after that is stopped.

Since the 98% duty control is performed and the operation for forcedly turning off the heater is performed in a period during which the full turn-on control is inherently executed, the values of Voff and Ioff can be detected when the trouble occurrence is temporarily discriminated. Consequently, the trouble in the heater control system can be accurately grasped and an inconvenience such as an excessive rise in the sensor temperature is not caused.

When the malfunction indicator light 42 is turned on as described above, the vehicle in which the trouble occurs is brought in a repair shop or the like in accordance with the warning. When the trouble information stored in the back-up RAM 20*d* is read by a diagnosis checker or the like, the trouble location can be easily specified without needing complicated work and a repair work according to the trouble is made.

According to the embodiment of the invention described above in detail, the following advantages can be provided.

(a) In the embodiment, the four values of the voltage Von and the current Ion when the heater 33 is turned on and the voltage Voff and the current Ioff when the heater 33 is not turned on are respectively compared with the predetermined thresholds Vth and Ith, the presence or absence of the trouble is discriminated according to which one of the compared four values is different from the value in the normal state, and the troubled location is specified. That is, when the trouble in the heater control system occurs, the trouble occurrence can be accurately discriminated and the troubled location can be also specified in detail. In this case, by using the result of the specification of the troubled location, the work to specify the troubled location necessary to be performed by an actual repair can be largely simplified. As a result, an advantage that the maintenance performance and the workability is improved can be also obtained.

(b) In the embodiment, by specifying the various troubles as shown in FIG. 15 every occurrence location or every mode, the trouble discrimination corresponding to a real machine can be realized.

(c) In the beginning of the turn-on of the heater 33 with the start of the engine, the heater off-voltage Voff and the heater off-current Ioff are detected prior to the start of the full turn-on control. After detecting Voff and Ioff, the turn-on of the heater 33 is started and the heater on-voltage Von and the heater on-current Ion are detected (initial processing of FIG. 6). The trouble discrimination is performed in accordance with the detected values Voff, Ioff, Von, and Ion. In this case, when the full turn-on control of the heater 33 is performed (when Duty=100%), even if a trouble occurs, Voff and Ioff cannot be detected, so that the trouble discrimination cannot be accurately performed. By detecting Voff and Ioff before starting the turn-on, however, the four values of Von, Ion, Voff and Ioff can be detected. Consequently, the desired trouble discrimination as described above can be performed.

(d) When the trouble occurrence is discriminated in the beginning of the start of the heater turn-on, the "98% Duty control" is performed to stop the heater on-state for the minimum time in which Voff and Ioff can be detected (step 106 in FIG. 5). If the occurrence of the trouble in the heater control system is continuously discriminated in such a state for a predetermined time or longer, the trouble occurrence is determined finally (steps 216 to 220 in FIG. 9). In this case, erroneous discrimination can be avoided during the temporary trouble discrimination in the beginning of the start of the engine, so that the trouble can be more accurately discriminated.

(e) Further, in the embodiment, the control duty ratio Duty is limited by the predetermined lower limit guard value (1%) (steps 112, 113 in FIG. 5). In this case, even when the exhaust temperature is high and the heater does not have to be turned on (when Duty=0%), for example, at the time of high load operation of the engine 10 or the like, the heater on-voltage Von and the heater on-current Ion can be certainly detected. Consequently, the four values of Von, Ion, Voff and Ioff can be continuously detected and the desired trouble discrimination as described above can be performed.

(f) If the trouble in the heater control system can be accurately grasped as described above, the normal active state of the A/F sensor 30 can be maintained. As a result, the air-fuel ratio F/B control with high precision can be performed, the emission is reduced, and regulations regarding emission control can be properly dealt with.

(Modification of First Embodiment)

The above first embodiment may be modified as follows.

[1] Although the value of voff is compared with the second threshold voltage Vth2 at the time of a trouble when the following four conditions are satisfied;

Von>Vth,

Ion<Ith,

Voff>Vth, and

Ioff<Ith, (in case of YES in step 208 in FIG. 8) in the routine (FIGS. 7 to 9) for discriminating the trouble in the heater control system to thereby discriminate trouble of the opening of the C-part and the D-part and the trouble of the short-circuit between D, E, F −GND short-circuit (step 209 in FIG. 8) in the embodiment, the construction may be changed. For example, the process of step 209 is omitted and when the step 208 is affirmatively discriminated, it may be concluded that the trouble due to "the opening of the C-part or the D-part or the short-circuit between D, E, F −GND" occurs.

It is also possible that the number of times of the locations or modes for discriminating the trouble is reduced to reduce the processing load of the CPU 20a (FIG. 15). Specifically, the frequency of occurrence of the trouble or priority order is considered and all or A-part of the troubles due to the E-part opening, the F-part opening, the G-part opening in FIG. 4, continuous ON state and continuous OFF state of the MOS 26 can be excluded from the target of the trouble discrimination. In short, the troubles due to the A-part opening, the B-part opening, the C-part opening, and the D-part opening, and the short-circuit between D, E, F −GND in FIG. 4 are set to targets indispensable to be discriminated. In this case, the trouble having high occurrence frequency or the trouble having the high priority can be properly discriminated. In the case where most of the causes of the troubles are due to the ON/OFF trouble of the semiconductor switching device, the target of the trouble to be discriminated can be limited to the ON/OFF trouble of the switching device.

[2] In the embodiment, the full turn-on control of the heater 33 is performed in the beginning of the low-temperature start of the engine 10. That is, the heater 33 is heated by the 100% turn-on. The construction can be changed so as to limit the control duty ratio of the heater 33 by, for example, the upper limit guard value of "98%". In this case, it is unnecessary to separately perform the "full turn-on control" and the "98% turn-on control" before the activation of the sensor as in the heater control routine of FIG. 5. According to the construction, the upper and lower limits of the control duty ratio are limited in a range "from 1% to 98%" and the values of Von, Ion, Voff, and Ioff can be continuously detected. The limitation of the duty ratio by using the upper and lower limit guards is not an essential condition in the invention. The invention can be embodied by properly omitting the limitation.

[3] Although the occurrence of the trouble is temporarily discriminated in the beginning of the start of the turn-on of the heater and it is determined when such a state continues more than a predetermined time in the embodiment (steps 216 to 220 in FIG. 9), the process of the temporary discrimination can be also applied besides the beginning of the start of the turn-on of the heater. In this case, the erroneous discrimination of the occurrence of the trouble can be prevented. On the contrary, in order to simplify the operating process, the invention can be also embodied while eliminating the process of the temporary discrimination.

Figure 16:
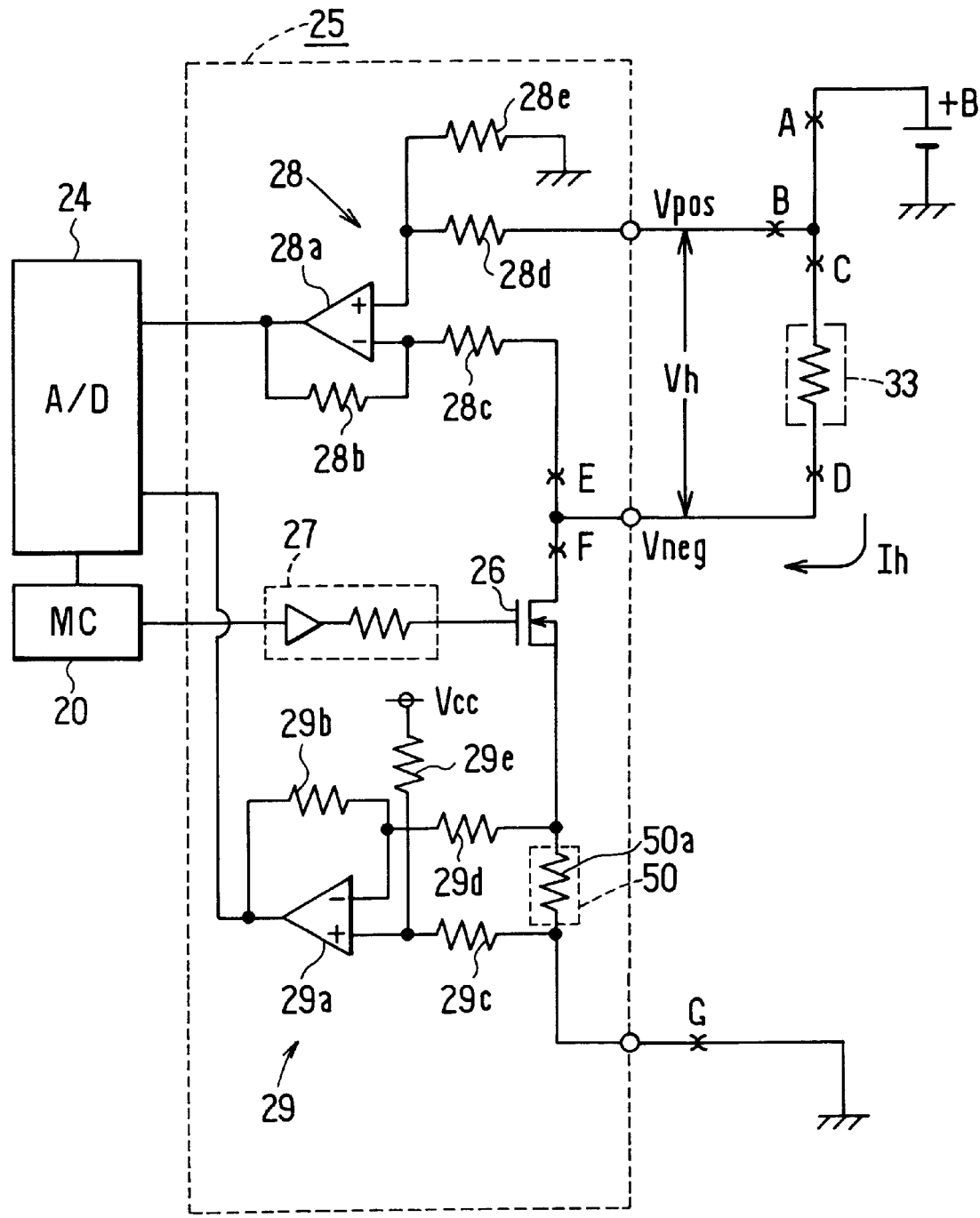
FIG. 16 is a circuit diagram showing a modification of the heater control circuit used in the first embodiment.

[4] The construction of the heater control circuit 25 may be changed as shown in FIG. 16. Specifically, the construction of the heater current detection circuit 29 is changed. The heater current detection circuit 29 in FIG. 16 is constructed by the differential amplifying circuit comprising the operational amplifier 29a, resistors 29c, 29e and a constant voltage power source Vcc (5 volts) connected to the non-inverting input terminal of the operational amplifier 29a, and resistors 29b and 29d connected to the inverting input terminal. The detection circuit 29 converts the heater current Ih detected by the resistor 50a for heater current detection into a voltage signal and outputs the result to the microcomputer 20 via the A/D converter 24. The construction has, differently from the construction of FIG. 4, an output characteristic such that the larger the heater current Ih is, the smaller the output of the operational amplifier 29a becomes.

Figure 17:
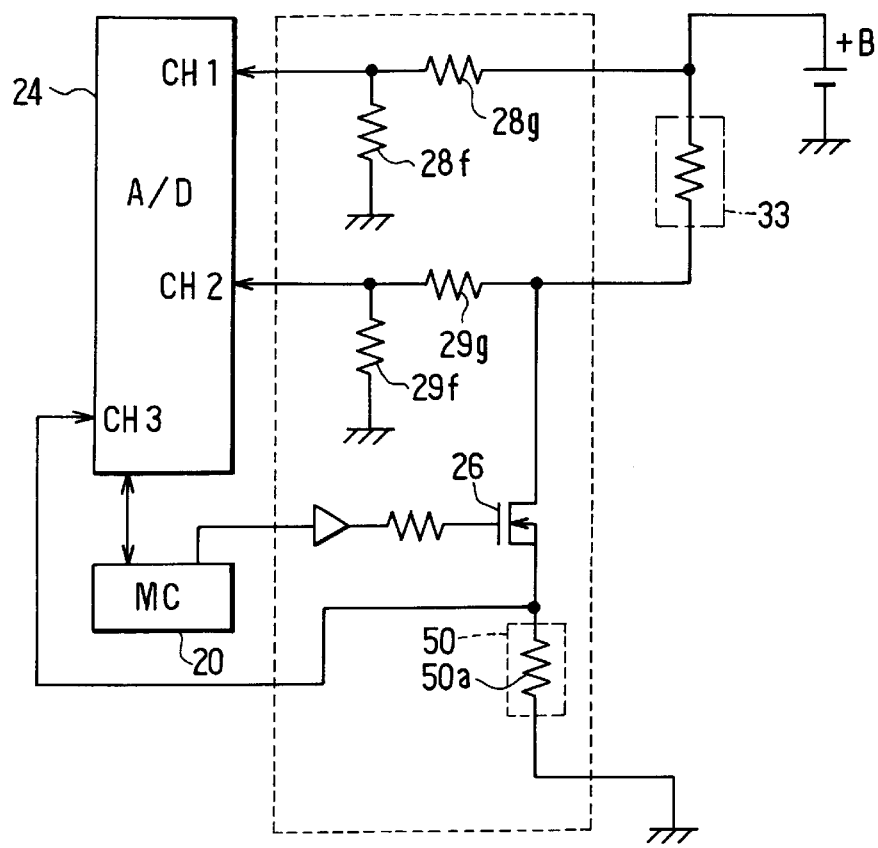
FIG. 17 is a circuit diagram showing another modification of the heater control circuit used in the first embodiment.

[5] In the heater control circuit of FIG. 17, the voltage detection circuit 28 and the current detection circuit 29 are constructed by the A/D converter 24 and the microcomputer 20. In the construction, a potential on the battery side of the heater 33 is inputted to "CH1" of the A/D converter 24 via resistors 28f and 28g and a potential on the GND side of the heater 33 is inputted to "CH2" of the A/D converter 24 via resistors 29f and 29g. A potential on the heater side of the resistor 50a for heater current detection is inputted to "CH3" of the A/D converter 24. The microcomputer 20 detects voltages (Von, Voff) on the both ends of the heater 33 and the heater currents (Ion, Ioff) on the basis of the signals inputted to CH1, CH2, and CH3 of the A/D converter 24.

[6] The heater control circuit 25 can be constructed by combining the circuits shown FIGS. 4, 16, and 17. Further, the construction of the heater current low side detection or the construction of the heater current high side detection can be applied. Those circuit constructions can be selectively used in accordance with design concept and the like of each engine.

[7] The thresholds for comparing and discriminating the detection values (Von, Ion) of the voltage and the current in the on-state of the heater 33 and the thresholds for comparing and discriminating the detection values (Voff, Ioff) of the voltage and the current in the off-state of the heater 33 may be also separately provided. That is, in the construction of the embodiment, Von=11 volts, Ion=5 amperes, Voff=0 volt, Ioff=0 ampere or a value close to 0 ampere when the heater control system is normal. For example, it may be set as follows:

the threshold voltage (Vthon) in the heater on-state is about "9 volts", the threshold current (Ithon) in the heater on-state is about "4 amperes", the threshold voltage (Vthoff) in the heater off-state is about "2 volts", and the threshold current (Ithoff) in the heater off-state is about "1 ampere".

It is discriminated that the heater control system is normal only when the following four conditions are satisfied:

Von>Vthon,
Ion>Ithon,
Voff<Vthoff, and
Ioff<Ithoff.

In other cases, the location and mode of the trouble of the heater control system are specified with reference to FIG. 15 in accordance with the relation between the four detection values (Von, Ion, Voff, and Ioff) and the four thresholds. With the construction, the trouble can be more accurately discriminated.

[8] Although the limit-current type sensor (A/F sensor) 30 is used in the embodiment, it can be also realized by using other types of oxygen sensors. For example, the an $O_2$ sensor for outputting a voltage signal (electromotive force) which changes its output level between high and low according to whether the oxygen is present or not in the exhaust gas.

Further, the sensor 30 may be used to detect oxygen concentration in any gas other than the exhaust gas.

Further, the trouble detection may be applied to any other sensors as long as the sensor is responsive to gas concentration and is of the type which is to be heated by the heater for activation.

(Second Embodiment)

Figure 18:
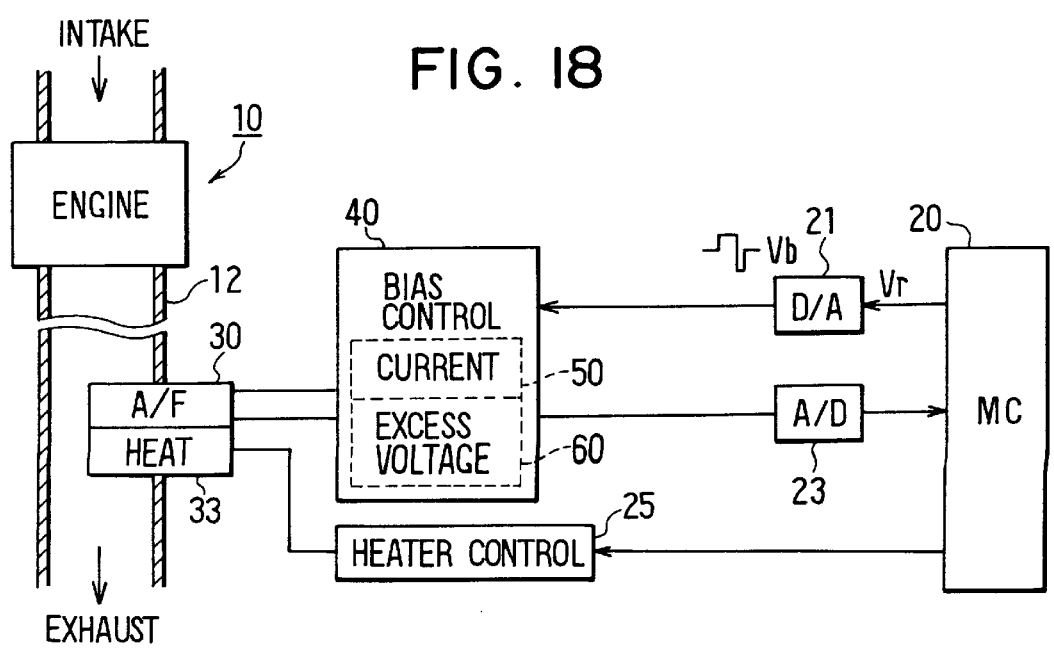
FIG. 18 is a block diagram showing an air-fuel ratio detection apparatus according to the second embodiment of the present invention.

The second embodiment shown in FIG. 18 is directed to detect excess current flow through the A/F sensor 30 (FIGS. 2 and 3) and constructed similarly to the first embodiment shown in FIG. 1. However, in the second embodiment, the bias control circuit 40 is provided with an excess voltage detection circuit 60 in addition to the current detection circuit 50 to detect malfunction of the voltage applied to the A/F sensor 30.

Figure 19:
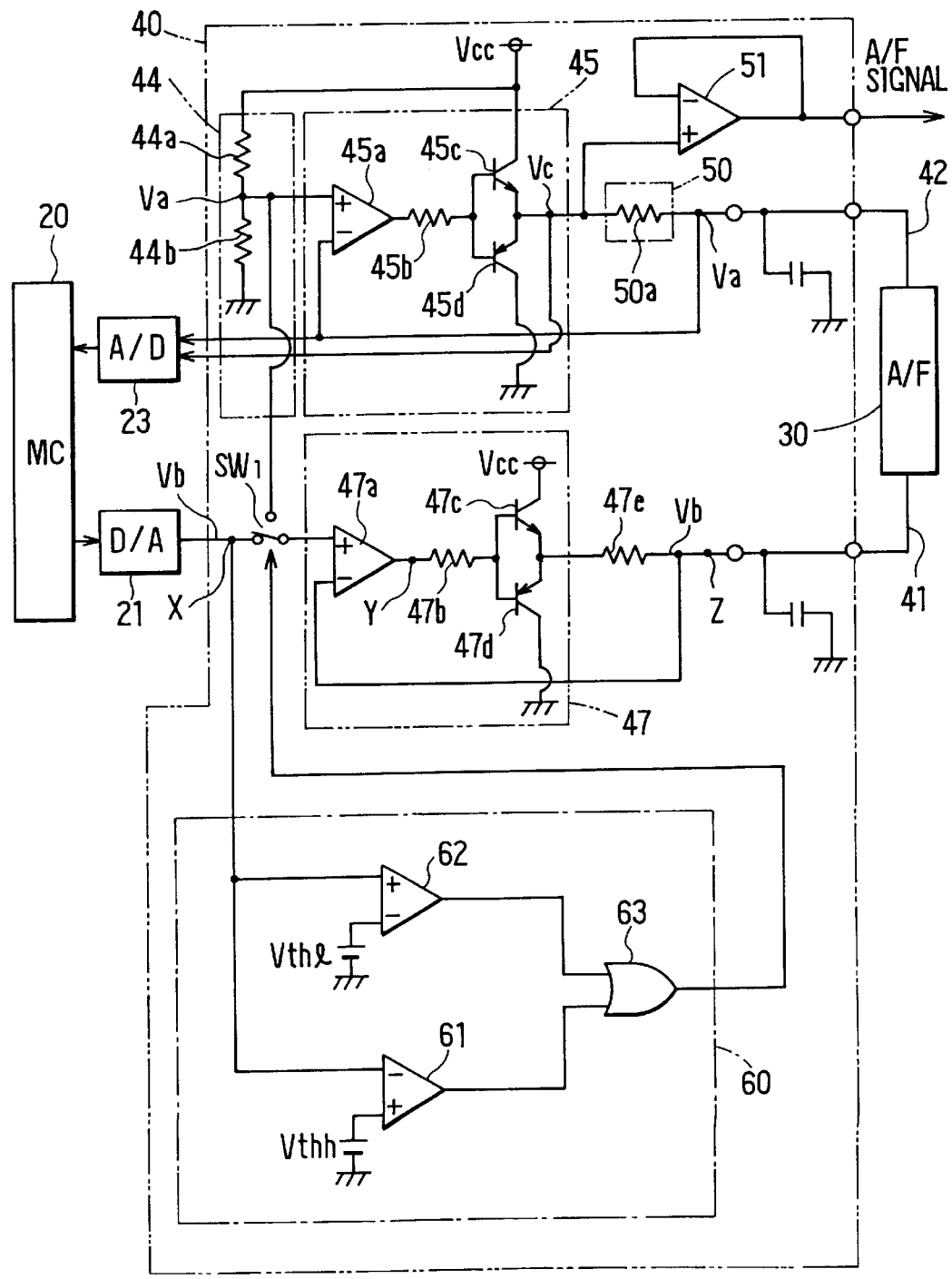
FIG. 19 is a circuit diagram showing a bias control circuit used in the second embodiment.

The bias control circuit 40 including the excess voltage detection circuit is constructed as shown in FIG. 19. In FIG. 19, the bias control circuit 40 has mainly a reference voltage circuit 44, a first voltage supplying circuit 45, a second voltage supplying circuit 47, the current detection circuit 50, and the excess voltage detection circuit 60. In the reference voltage circuit 44, a constant voltage Vcc is divided by voltage dividing resistors 44a and 44b, thereby providing a predetermined reference voltage Va.

The first voltage supplying circuit 45 is constructed by a voltage follower circuit and a voltage which is equal to the reference voltage Va of the reference voltage circuit 44 is supplied from the first voltage supplying circuit 45 to a positive-side terminal 42 of the A/F sensor 30. More specifically, the circuit 45 is constructed by: an operational amplifier 45a the non-inverting input terminal of which is connected to a voltage dividing point of the voltage dividing resistors 44a and 44b and the inverting input terminal of which is connected to the terminal 42 of the A/F sensor 30; a resistor 45b one end of which is connected to the output terminal of the operational amplifier 45a; and an NPN transistor 45c and a PNP transistor 45d the bases of which are connected to the other end of the resistor 45b. The collector of the NPN transistor 45c is connected to the constant voltage Vcc and the emitter is connected to the terminal 42 of the A/F sensor 30 via the current detection resistor 50a of the current detection circuit 50. The emitter of the PNP transistor 45d is connected to the emitter of the NPN transistor 45c and the collector is connected to the ground.

The second voltage supplying circuit 47 is similarly constructed by a voltage follower circuit and a voltage Vb which is equal to the output voltage Vb of the D/A converter 21 is supplied to the ground-side terminal 41 of the A/F sensor 30. More specifically, it is constructed by: an operational amplifier 47a the non-inverting input terminal is connected to the output of the D/A converter 21 via a change-over switch SW1 and the inverting input terminal is connected to the terminal 41 of the A/F sensor 30; a resistor 47b one end of which is connected to the output terminal of the operational amplifier 47a; and an NPN transistor 47c and a PNP transistor 47d the bases of which are connected to the other end of the resistor 47b. The collector of the NPN transistor 47c is connected to the constant voltage Vcc and the emitter is connected to the other terminal 41 of the A/F sensor 30 via a resistor 47e. The emitter of the PNP transistor 47d is connected to the emitter of the NPN transistor 47c and the collector is connected to the ground.

With the reference voltage Va being continuously supplied to the terminal 42 of the A/F sensor 30, when the voltage Vb lower than the reference voltage Va is applied to the terminal 41 of the A/F sensor 30 via the D/A converter 21 to provide a voltage Vp changing linearly along line L1 in FIG. 3, the A/F sensor 30 is positively biased. When the voltage Vb switched to be higher than the reference voltage Va is applied to the terminal 41 of the A/F sensor 30 via the D/A converter 21 to provide the voltage Vp changing linearly along the line L1, the A/F sensor 30 is negatively biased.

The sensor current (limit-current) flowing with the application of the voltage is detected as a potential difference across the current detection resistor 50a and is inputted to the microcomputer 20 via the A/D converter 23. An output buffer 51 is connected to the current detection circuit 50. The A/F (air-fuel ratio) detected by the A/F sensor 30 is directly extracted from the output buffer 51.

Further, the output voltage Vb of the D/A converter 21 is applied to the excess voltage detection circuit 60, i.e., both of the inverting input terminal of a comparator 61 and the non-inverting input terminal of a comparator 62. A comparison reference voltage Vthh on the high voltage side is inputted to the non-inverting input terminal of the comparator 61 and a comparison reference voltage Vthl on the low voltage side is inputted to the inverting input terminal of the comparator 62. Outputs of the comparators 61 and 62 are inputted to an OR gate 63. By an output from the OR gate 63, the change-over switch SW1 connected between the D/A converter 21 and the non-inverting input terminal of the operational amplifier 47a in the second voltage supplying circuit 47 is changed.

In operation of the second embodiment, as long as the output voltage Vb of the D/A converter 21 lies within a normal voltage zone between the comparison voltage Vthh and the comparison voltage Vthl, the change-over switch SW1 is held in the change-over position shown in FIG. 19 by a high level output of the OR gate 63, thereby connecting the D/A converter 21 and the non-inverting input terminal of the operational amplifier 47a in the second voltage supplying circuit 47. On the other hand, when the output voltage Vb of the D/A converter 21 is out of the normal zone between the comparison voltages Vthh and Vthl, the change-over switch SW1 is changed by a low level output from the OR gate 63 in the excess voltage detection circuit 60, so that the D/A converter 21 and the non-inverting input terminal of the operational amplifier 47a in the second voltage supplying circuit 47 are opened, the non-inverting input terminal of the operational amplifier 47a in the second voltage supplying circuit 47 and the non-inverting input terminal of the operational amplifier 45a in the first voltage supplying circuit 45 are connected, so that both of the terminals 41 and 42 of the A/F sensor 30 have the same potential, thereby protecting the A/F sensor 30.

Although the voltage inputted to the inverting input terminal of the comparator 61 in the excess voltage detection circuit 60 and the non-inverting input terminal of the comparator 62 is the input voltage Vb at the X-point on the D/A converter 21 side of the change-over switch SW1 in the bias control circuit 40, a voltage at the Y-point on the output terminal side of the operational amplifier 47a in the second voltage supplying circuit 47 in the bias control circuit 40 may be also used. Further, the voltage Vb applied to the Z-point on the terminal 41 side of the A/F sensor 30 in the bias control circuit 40 may be also used.

As shown in FIG. 19, when the voltage from the X-point in the bias control circuit 40 is inputted to the excess voltage detection circuit 60, the A/F sensor 30 is protected from output abnormality of the microcomputer 20 and output abnormality of the D/A converter 21 due to erroneous operation of the microcomputer 20 or instability in the initial process. When the voltage from the Y-point in the bias control circuit 40 is applied to the excess voltage detection circuit 60, the A/F sensor 30 is protected further from output abnormality of the operational amplifier 47a in the second voltage supplying circuit 47. Further, when the voltage from the Z-point in the bias control circuit 40 is applied to the excess voltage detection circuit 60, the A/F sensor 30 is protected still further from output abnormality of the operational amplifier 47a in the second voltage supplying circuit 47, output abnormality of the F/B (feedback) control system, and an excessive voltage due to noises superimposed on a sensor power supply line or the like.

As described above, according to the second embodiment, when the voltage applied to the A/F sensor 30 is detected to be outside the normal voltage zone by the excess voltage detection circuit 60, the excessive current does not flow in the sensor element thereby protecting the A/F sensor 30 from deteriorating due to the excessive current flow. The excessive voltage may occur in a period during which an output of the microcomputer 20 which calculates the voltage Vb and hence Vp across the A/F sensor 30 is changing or when the microcomputer 20 detects disconnection or short-circuit of component elements.

(Modification of Second Embodiment)

The second embodiment may be modified as follows.

Figure 20:
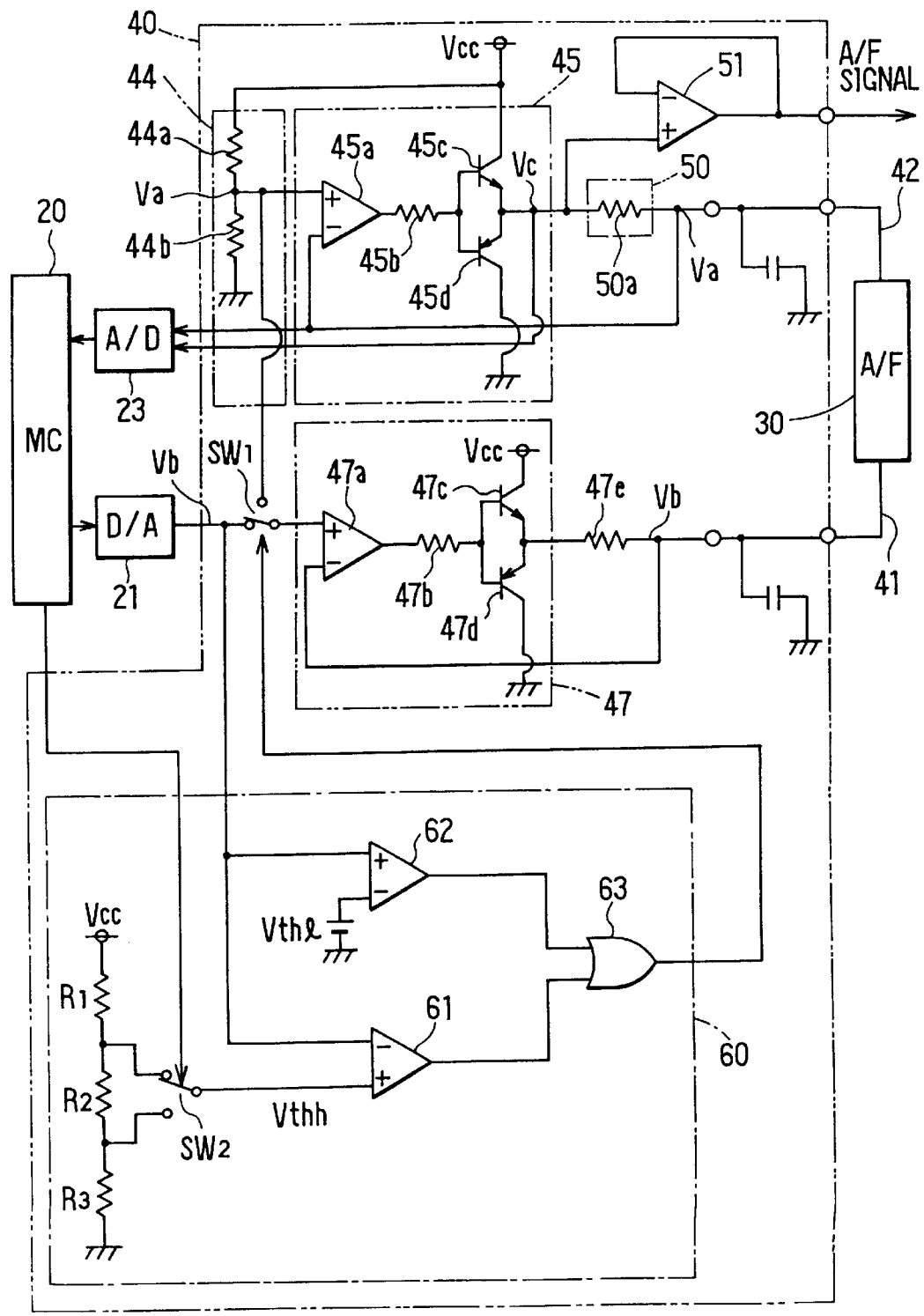
FIG. 20 is a circuit diagram showing a modification of the bias control circuit used in the second embodiment.

[1] In one modification shown in FIG. 20, the comparison voltage Vthh on the high voltage side applied to the non-inverting input terminal of the comparator 61 in the excess voltage detection circuit 60 is set to voltages of two stages provided by dividing the constant voltage Vcc by voltage dividing resistors R1, R2, and R3. By controlling the change-over switch SW2 by the microcomputer 20, a comparison voltage of either one of the voltages at two stages is applied to the non-inverting input terminal of the comparator 61. Thus, a plurality of abnormal voltages corresponding to the A/F can be dealt with. When the voltage applied to the A/F sensor 30 is out of the normal voltage zone, by setting the both terminals 41 and 42 of the A/F sensor 30 to have the same potential, the A/F sensor 30 is protected from deterioration since no excess current flows in the sensor element. By increasing the number of voltage dividing resistors and the number of terminals of the change-over switch, the voltage can be changed over at more stages and more fine setting of the comparison voltage can be realized. A plurality of the comparison voltages can be also set in the negative side input terminal of the comparator 62.

Figure 21:
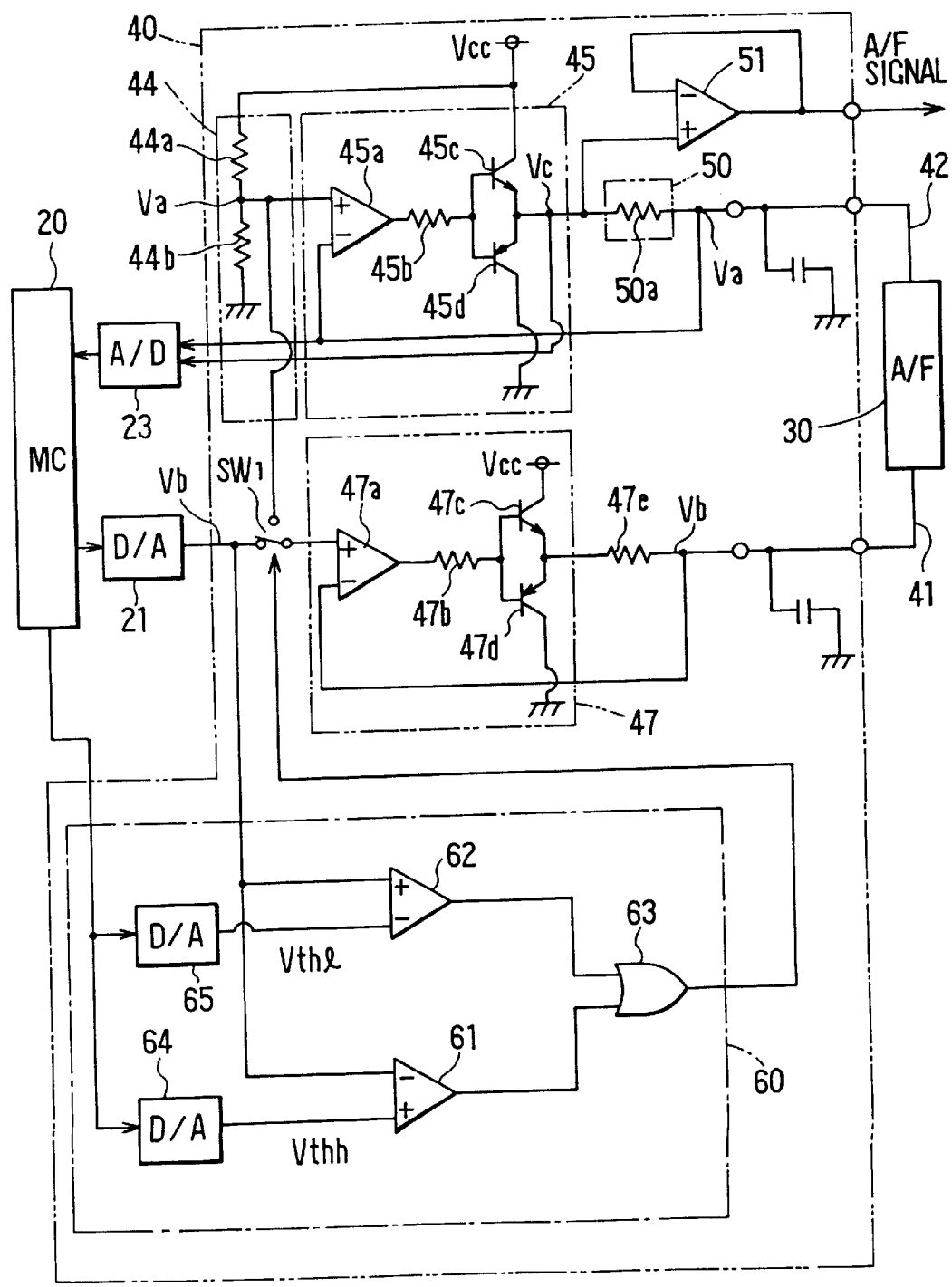
FIG. 21 is a circuit diagram showing another modification of the bias control circuit used in the second embodiment.

[2] In another modification shown in FIG. 21, in the excess voltage detection circuit 60, a D/A converter 64 is connected to the non-inverting input terminal of the comparator 61 so that the comparison voltage Vthh on the high voltage side can be arbitrarily set by the microcomputer 20 via the D/A converter 64. A D/A converter 65 is connected to the inverting input terminal of the comparator 62 so that the comparison voltage Vthl on the low voltage side can be arbitrarily set by the microcomputer 20 via the D/A converter 65.

Figure 22:
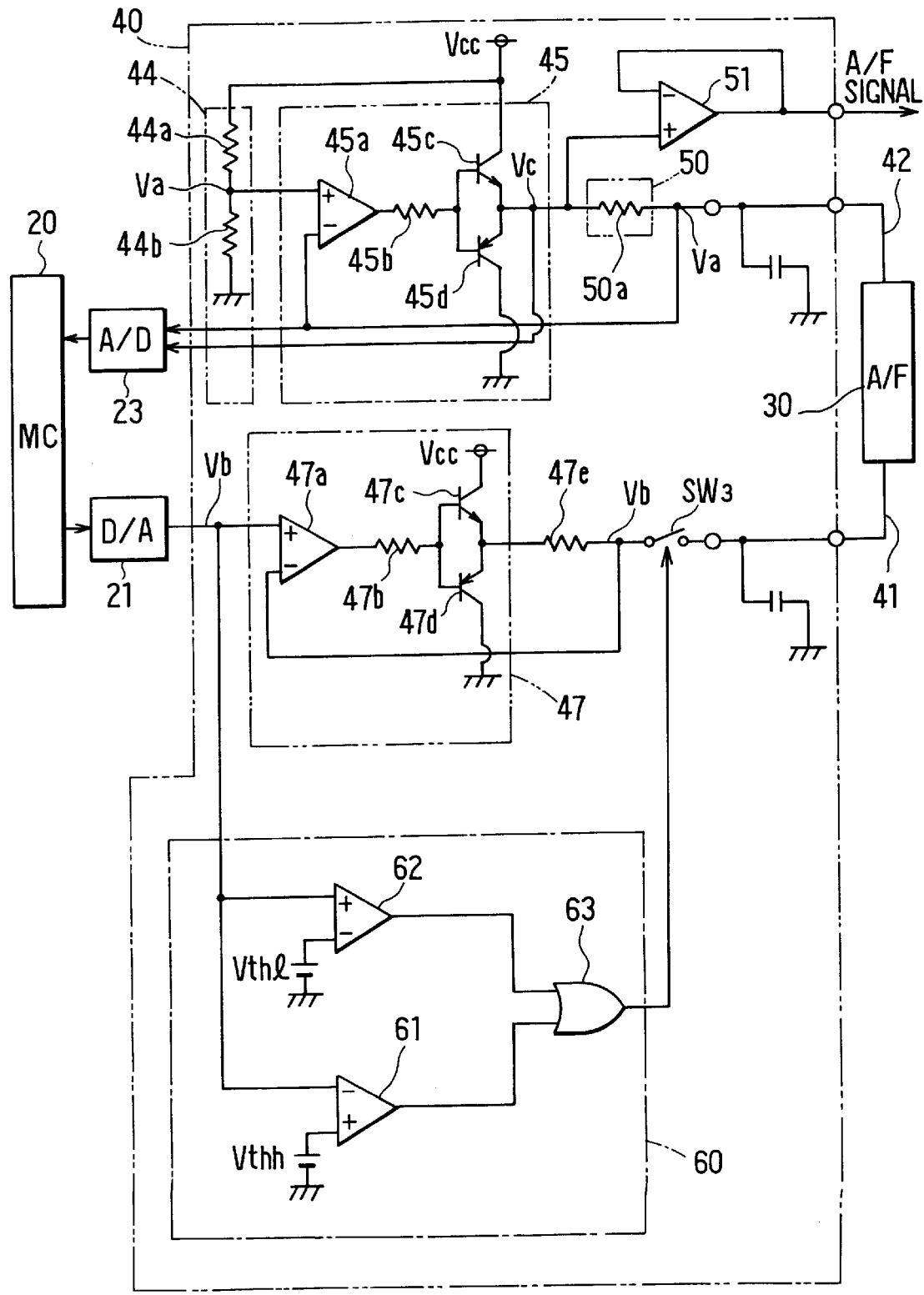
FIG. 22 is a circuit diagram showing the other modification of the bias control circuit used in the second embodiment.

[3] In a further modification shown in FIG. 22, the D/A converter 21 and the non-inverting input terminal of the operational amplifier 47a in the second voltage supplying circuit 47 is connected directly without a change-over switch. Instead, an ON/OFF switch SW3 is provided on the terminal 41 side of the A/F sensor 30. The ON/OFF switch SW3 is turned ON (connected)/OFF (opened) in response to an output the OR gate 63 in the excess voltage detection circuit 60.

In the event of malfunction in which the output voltage Vb from the D/A converter 21 is out of the zone between the comparison voltage Vthh on the high voltage side and the comparison voltage Vthl on the low voltage side, the ON/OFF switch SW3 is turned off, thereby setting the both terminals 41 and 42 of the A/F sensor 30 to have the same potential.

The ON/OFF switch SW3 may be provided on the terminal 42 side of the A/F sensor 30 and the reference voltage Va side may be opened when excess voltage is detected.

Figure 23:
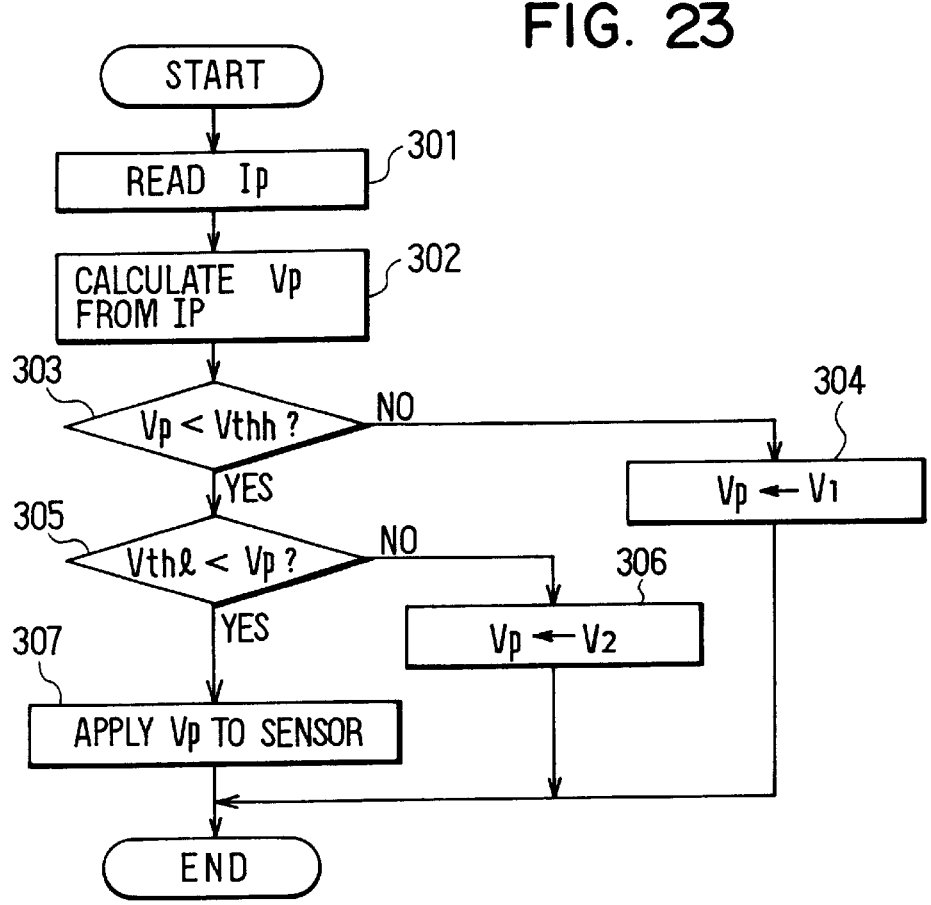
FIG. 23 is a flowchart showing a routine for setting an application voltage to the A/F sensor in a further modification of the second embodiment.
Figure 24:
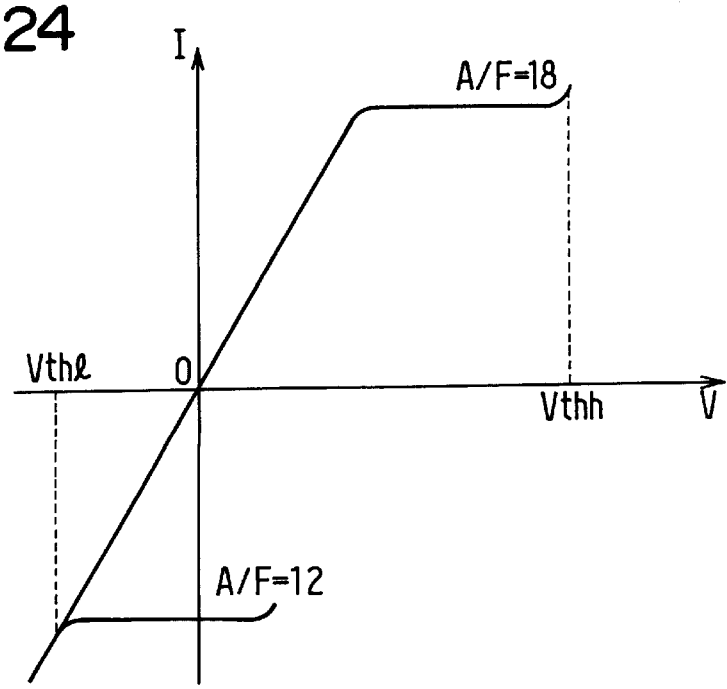
FIG. 24 is a V-I output characteristics of the A/F sensor in the modification of FIG. 23.

[4] In a further modification shown in FIGS. 23 and 24, the microcomputer 20 is programmed to detect the excess voltage without using the excess voltage detection circuit 60 shown in FIGS. 19 to 22.

In this modification, the sensor current Ip flowing in the A/F sensor 30 with application of the voltage Vp is detected as a potential difference across the current detection resistor 50a in the current detection circuit 50 and is read through the A/D converter 23 in step 301. The processing routine advances to step 302 and the application voltage Vp to be applied to the A/F sensor 30 is calculated from the sensor current Ip read in step 301 and is stored in the RAM. The processing routine advances to step 303 and it is discriminated whether the application voltage Vp stored in the RAM in step 302 is lower than, for example, as shown by the voltage-current characteristics of FIG. 24, the upper limit discriminating voltage Vthh which is set so as to be slightly higher than an application voltage zone corresponding to the sensor current of A/F=18 which is preliminarily set in the ROM. When the discrimination condition in step 303 is not satisfied and the voltage Vp is not lower than the upper limit discriminating voltage Vthh, the applied voltage Vp is discriminated as abnormal. The processing routine advances to step 304 and an upper limit voltage V1 preliminarily stored in the ROM is stored as an application voltage Vp in the RAM in order to protect the A/F sensor 30.

On the other hand, when the discrimination condition in step 303 is satisfied, the processing routine advances to step 305. It is discriminated whether the applied voltage Vp stored in the RAM in step 302 is higher than, for example, as shown by the voltage-current characteristic of FIG. 24, the lower limit discriminating voltage Vthl or not which is set so as to be slightly lower than the application voltage zone corresponding to the sensor current of A/F=12 preliminarily stored in the ROM. When the discrimination condition in step 305 is not satisfied and the applied voltage Vp is not higher than the lower limit discriminating voltage Vthl, the applied voltage Vp is discriminated as abnormal and the processing routine advances to step 306. A lower limit voltage V2 preliminarily stored in the ROM is stored as the applied voltage Vp in the RAM in order to protect the A/F sensor 30. After the process of step 304 or 306 or when the discrimination condition in step 305 is satisfied and the original applied voltage Vp is a normal value, the processing routine advances to step 307 and the voltage Vp stored in the RAM is applied to the sensor element of the A/F sensor 30, thereby finishing the routine.

Thus, when the calculated voltage lies outside of the predetermined zone, the application voltage Vp in the RAM is forcedly updated to the upper limit voltage V1 or the lower limit voltage V2 as predetermined values. That is, when the application voltage Vp in the RAM calculated and stored by the microcomputer 20 every predetermined cycle is compared with the upper limit discriminating voltage Vthh and the lower limit discriminating voltage Vthl and the application voltage Vp is discriminated as abnormal, the value is restricted differently from the calculated value to the upper limit voltage V1 or the lower limit voltage V2 as predetermined values. Consequently, a proper voltage is applied to the A/F sensor 30. Since no excess current does not flow in the sensor element, the A/F sensor 30 is protected from deterioration.

Figure 25:
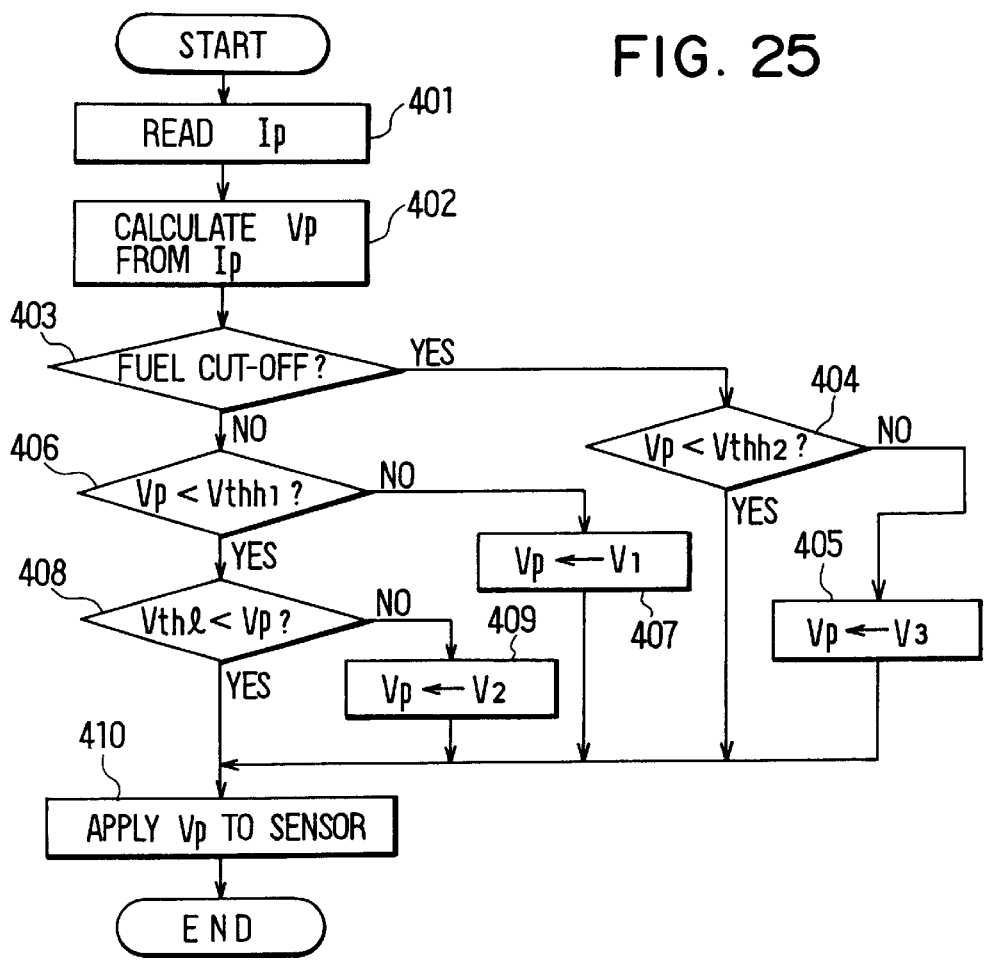
FIG. 25 is a flowchart showing a still further modification of the second embodiment.
Figure 26:
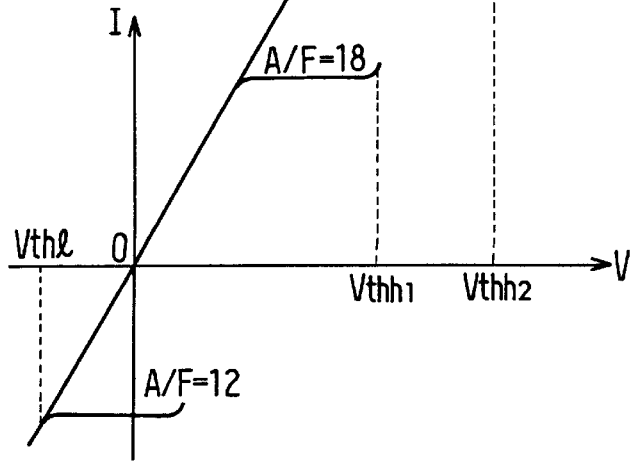
FIG. 26 is a V-I output characteristics of the A/F sensor in the modification of FIG. 25.

[5] In a still further modification shown in FIGS. 25 and 26, the microcomputer 20 is programmed to detect the malfunction as follows.

In step 401, the sensor current Ip flowing in the A/F sensor 30 with the application of the voltage is detected as a potential difference across the current detection resistor 50a in the current detection circuit 50 and is read via the A/D converter 23. The processing routine advances to step 402 and a present application voltage Vp to the A/F sensor 30 is calculated from the sensor current Ip read in step 401 and is stored in the RAM. The processing routine advances to step 403 and whether it is during fuel cut-off or not is discriminated on the basis of the sensor current Ip read at the A/F detection timing. When the discrimination condition in step 403 is satisfied and it is during the fuel cut-off, the processing routine advances to step 404. Whether the application voltage Vp stored in the RAM in step 402 is lower than, for example, as shown by the voltage-current characteristics of FIG. 26, the upper limit discriminating voltage Vthh2 which is preliminarily stored in the ROM and is set slightly higher than the application voltage zone corresponding to the sensor current in atmosphere (during the fuel cut-off) or not is discriminated. When the discrimination condition in step 404 is not satisfied and the application voltage Vp is not lower than the upper limit discriminating voltage Vthh2, the application voltage Vp is discriminated as abnormal. The processing routine advances to step 405 and the upper limit voltage V3 preliminarily stored in the ROM is stored as the application voltage Vp in the RAM in order to protect the A/F sensor 30.

On the other hand, when the discrimination condition in step 403 is not satisfied and it is not during the fuel cut, the processing routine advances to step 406. Whether the application voltage Vp stored in the RAM in step 402 is lower than, for example, as shown by the voltage-current characteristics of FIG. 26, the upper limit discriminating voltage Vthh1 which is preliminarily stored in the ROM and is set slightly higher than the application voltage zone corresponding to the sensor current A/F=18 or not is discriminated. When the discrimination condition in step 406 is not satisfied and the application voltage Vp is not lower than the upper limit discriminating voltage Vthh1, the application voltage Vp is discriminated as abnormal and the processing routine advances to step 407. The upper limit voltage V1 preliminarily stored in the ROM is stored as the application voltage Vp in the RAM in order to protect the A/F sensor 30.

On the other hand, when the discrimination condition in step 406 is satisfied and the application voltage Vp is lower than the upper limit discriminating voltage Vthh1, the processing routine advances to step 408. Whether the application voltage stored in the RAM in step 402 is higher than the lower limit discriminating voltage Vthl which is preliminarily stored in the ROM and is set slightly lower than, for example, as shown by the voltage-current characteristics of FIG. 26, the application voltage zone corresponding to the sensor current of A/F=12 or not is discriminated. When the discrimination condition in step 408 is not satisfied and the application voltage Vp is not higher than the lower limit discriminating voltage Vthl, the application voltage Vp is discriminated as abnormal and the processing routine advances to step 409. The lower limit voltage V2 preliminarily stored in the ROM is stores as an application voltage Vp in the RAM in order to protect the A/F sensor 30. When the discrimination condition in the step 404 or 408 is satisfied after the process of step 405, 407, or 409 and the original application voltage Vp is a normal value, the processing routine advances to step 410. The voltage Vp stored in the RAM is applied to the sensor element of the A/F sensor 30, thereby finishing the routine.

Thus, the microcomputer 20 changes the preset comparison value in accordance with the A/F (air-fuel ratio). That is, the preset comparison value is changed to a comparison value which corresponds to the present A/F by the microcomputer 20. Consequently, when the A/F detection zone is wide, for example, when the air-fuel ratio is set close to that of the atmospheric air during the fuel cut-off, since the zone of the voltage applied to the sensor element is also wide, it is necessary to widen the comparison value zone. However, a plurality of comparison values are preset and are changed according to the A/F and discriminated, thereby applying a proper voltage to the A/F sensor 30. Since no excess current flows in the sensor element, the A/F sensor 30 is protected from deterioration.

Although the above embodiments and modifications are applied to the oxygen-responsive sensor, the same may be applied to other types of gas concentration sensor which is responsive to nitrogen oxides (NOx), hydro carbon (HC) or carbon monoxide (CO) as long as it uses a hetaer for activating the sensor. Further, the present invention may be modified without departing from the spirit of the invention.

What is claimed is:

1. An apparatus for detecting trouble in a heater control system for a gas concentration sensor, the heater control system having a heater attached to the gas sensor and heater control means for turning electric power supplied to the heater on and off at a predetermined control duty-cycle ratio, the apparatus comprising:

voltage detecting means connected to the heater for detecting voltage across the heater when the electric power is turned on and when it is turned off;

current detecting means connected to the heater for detecting electric current flowing in the heater when the electric power is turned on and when it is turned off; and trouble discriminating means for comparing the four thus detected values of heater voltage and current with four respective predetermined thresholds and detecting the absence or presence and location in the circuit of trouble in accordance with which of the four detected values is different from a normal state.

2. The apparatus of claim 1, wherein:

the trouble discriminating means specifies at least one trouble due to opening of an electric circuit on a power source side of the heater and an electric circuit connecting a ground side of the heater.

3. The apparatus of claim 1, wherein:
the trouble discriminating means specifies trouble in an electric circuit connecting the heater and the voltage detecting means.

4. The apparatus of claim 1, wherein:
the heater control means includes a semiconductor switching device for connecting and disconnecting an electric circuit between the heater and an electrical ground in accordance with a duty-cycle control signal of the heater control means; and
the trouble discriminating means specifies trouble due to a short-circuit of an electric circuit on the ground side of the heater.

5. The apparatus of claim 1, wherein:
the heater control means includes a semiconductor switching device for connecting and disconnecting an electric circuit connecting the power source, the heater, and an electrical ground in accordance with a duty-cycle control signal of the heater control means; and
the trouble discriminating means detects trouble which disables the on/off operation of the semiconductor switching device.

6. The apparatus of claim 1, wherein:
the gas concentration sensor is an oxygen responsive type sensor disposed in an engine exhaust to detect an air-fuel ratio of mixture supplied to the engine;
the heater control means includes full turn-on means for initially setting the duty-cycle ratio of electric power supplied to the heater to 100% at engine start;
the heater control means includes initial value detecting means for detecting heater voltage and current before starting heater turn-on by the full turn-on means, and then for detecting heater voltage and current after starting heater turn-on; and
the trouble discriminating means detects trouble in accordance with the voltages and currents detected by the initial value detecting means.

7. The apparatus of claim 6, wherein:
the heater control means includes setting means for setting a control duty-cycle ratio so as to stop the heater on-state for a minimum time in which the heater voltage and current can be detected when the occurrence of the trouble is detected in accordance with the voltages and currents detected by the initial value detecting means; and
the trouble discriminating means includes final means for finally determining occurrence of trouble when the heater on-state is controlled at the control duty ratio which is set and the occurrence of trouble is continuously detected for a predetermined time.

8. The apparatus of claim 1, wherein:
the heater control means includes limit means for limiting the duty-cycle ratio to a predetermined lower limit guard value or an upper limit guard value.

9. A method of detecting trouble in a heater control system for a gas concentration sensor, the heater control system having a heater attached to the gas sensor and heater control means for turning electric power supplied to the heater on and off at a predetermined control duty-cycle ratio, the method comprising the steps of:
detecting voltage across the heater when the electric power is turned on and when it is turned off;
detecting electric current flowing in the heater when the electric power is turned on and when it is turned off; and
comparing each of the four thus detected values of heater voltage and current with predetermined respective thresholds to identify a trouble part of the system in accordance with such comparison results.

10. The method of claim 9, further comprising the steps of:
initially setting an initial duty cycle ratio of the electric power to the heater to 100% at engine start; and
the comparing step detecting the trouble in accordance with the heater voltages and currents detected when the heater is supplied with the electric power at the initial duty-cycle ratio.

11. An apparatus for detecting malfunction of a gas concentration sensor system having a gas concentration sensor, the apparatus comprising:
voltage applying means for applying voltage to the gas concentration sensor which in response, outputs a current signal according to the concentration of gas to be detected; and
voltage discriminating means for detecting whether the voltage applied to the gas concentration sensor lies within a predetermined voltage zone.

12. An apparatus for detecting malfunction of a gas concentration sensor system having a gas concentration sensor, the apparatus comprising:
calculating means for calculating a gas concentration sensor voltage which outputs a current signal according to the concentration of gas to be detected; and
protection means for applying the same potential to the gas concentration sensor during a period of time of malfunction in the system which includes at least one of: (i) changing of an output of the calculating means and (ii) disconnection or short-circuit in the system.

13. The apparatus of claim 12, wherein:
the protection means is disposed to connect one terminal of the gas concentration sensor to the other terminal of the gas concentration sensor when the voltage discriminating means detects that the voltage applied to the gas concentration sensor is outside of the predetermined voltage zone.

14. The apparatus of claim 12, wherein:
the protection means is disposed to open either one of both terminals of the gas concentration sensor when the voltage discriminating means detects that the voltage applied to the gas concentration sensor is outside of the predetermined voltage zone.

15. The apparatus of claim 11, further comprising:
calculating means having a memory for temporarily storing a value of the gas concentration sensor voltage,
comparing means for comparing the value in the memory with a preset comparison value in a predetermined cycle, and
updating means for forcedly updating the value in the memory to a predetermined limit value when the value in the memory is outside of the predetermined zone.

16. The apparatus of claim 15, wherein:
the calculating means changes the preset comparison value in accordance with air-fuel ratio.

17. A method for detecting malfunction of a gas concentration sensor system having a gas concentration sensor, the method comprising the steps of:
determining a gas concentration sensor voltage which produces a current signal according to concentration of gas to be detected;
discriminating whether the gas concentration sensor voltage lies within a predetermined voltage zone; and disabling application to the voltage to the sensor in response to the discriminating step detecting the voltage being outside of the predetermined voltage range.

18. The method of claim 17, wherein:

the determining step determines voltage actually applied to the sensor; and the disabling step applies no voltage across the sensor.

19. The method of claim 17, wherein:

the determining step calculates voltage from current actually flowing in the sensor; and the disabling step restricts the voltage to a limit value irrespective of the calculated voltage.

\* \* \* \* \*